US012584156B2

(12) United States Patent
Koseki et al.

(10) Patent No.: US 12,584,156 B2
(45) Date of Patent: Mar. 24, 2026

(54) METHOD FOR PRODUCING PROTEIN

(71) Applicant: AJINOMOTO CO., INC., Tokyo (JP)

(72) Inventors: Yasumichi Koseki, Kanagawa (JP); Takahiro Katayama, Kanagawa (JP); Yusuke Ooya, Kanagawa (JP); Fumi Ogata, Kanagawa (JP); Kiyoshi Hirakawa, Kanagawa (JP); Takuya Higuchi, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 985 days.

(21) Appl. No.: 17/730,750

(22) Filed: Apr. 27, 2022

(65) Prior Publication Data

US 2022/0251622 A1    Aug. 11, 2022

Related U.S. Application Data

(63) Continuation of application No. PCT/JP2020/041377, filed on Nov. 5, 2020.

(30) Foreign Application Priority Data

Nov. 5, 2019    (JP) ................................. 2019-200753

(51) Int. Cl.
*C12P 21/02*      (2006.01)
*C12N 5/00*       (2006.01)

(52) U.S. Cl.
CPC ............ *C12P 21/02* (2013.01); *C12N 5/0018* (2013.01); *C12N 2500/05* (2013.01); *C12N 2500/32* (2013.01); *C12N 2501/105* (2013.01); *C12N 2510/02* (2013.01)

(58) Field of Classification Search
CPC .................................................... C12N 5/0018
See application file for complete search history.

(56) References Cited

U.S. PATENT DOCUMENTS

| | | | | |
|---|---|---|---|---|
| 6,924,124 | B1 | 8/2005 | Singh | |
| 2008/0064068 | A1* | 3/2008 | Knudsen | ........ C12Y 304/21021 |
| | | | | 435/70.3 |

| | | | | |
|---|---|---|---|---|
| 2009/0124006 | A1* | 5/2009 | Fonta | ..................... C07K 14/59 |
| | | | | 435/360 |
| 2011/0137012 | A1 | 6/2011 | Katayama et al. | |
| 2017/0191025 | A1 | 7/2017 | Shimoni et al. | |

FOREIGN PATENT DOCUMENTS

| | | |
|---|---|---|
| CN | 102994441 A | 3/2013 |
| JP | 01-222793 A | 9/1989 |
| JP | 01-247097 A | 10/1989 |
| JP | 2017-510283 A | 4/2017 |
| WO | WO2007/077217 A2 | 7/2007 |
| WO | WO2008/033517 A2 | 3/2008 |
| WO | WO2008/033517 A3 | 3/2008 |
| WO | WO2008/033517 A9 | 3/2008 |
| WO | WO2008/136398 A1 | 11/2008 |
| WO | WO2011/134920 A1 | 11/2011 |
| WO | WO2011/134921 A1 | 11/2011 |

OTHER PUBLICATIONS

Office Action for Chinese Patent App. No. 202080076873.4 (May 6, 2024) with English language translation thereof.
Sato, S., et al., "Stimulation of monoclonal antibody production by human-human hybridoma cells with an elevated concentration of potassium or sodium phosphate in serum-free medium," CYTOTECHNOL. 1989;2:63-67.
Hashizume, H., et al., "Generation and production of human monoclonal antibodies," Nippon Nogeikagaku Kaishi, 1988, vol. 62, No. 10, pp. 1513-1516, with English language machine translation thereof.
International Search Report for PCT Patent App. No. PCT/JP2020/041377 (Dec. 28, 2020).
Extended European Search Report for European Patent App. No. 20885757.3 (Nov. 8, 2023).
Handl, A., "Development of M3C Strategies in Production Processes With CHO Cell Cultures to Prevent the Formation of Product Aggregation," Dissertation, Jul. 1, 2019, XP093095837A, pp. 1-181, retrieved from the Internet: URL: https://oparu.uni-ulm.de/xmlui/bitstream/handle/123456789/19305/Dissertation_Handl.pdf?sequence=8&isAllowed=y [retrieved on Oct. 27, 2023].

* cited by examiner

*Primary Examiner* — Suzanne M Noakes
(74) *Attorney, Agent, or Firm* — Cermak & McGowan LLP; Shelly Guest Cermak

(57)        ABSTRACT

A method for producing an objective protein using animal cells as an expression host is provided. The objective protein is produced by culturing animal cells having an objective protein-producing ability under conditions where the phosphoric acid concentration and/or the potassium concentration in the culture medium is increased.

22 Claims, 7 Drawing Sheets

METHOD FOR PRODUCING PROTEIN

This application is a Continuation of, and claims priority under 35 U.S.C. § 120 to, International Application No. PCT/JP2020/041377, filed Nov. 5, 2020, and claims priority therethrough under 35 U.S.C. § 119 to Japanese Patent Application No. 2019-200753, filed Nov. 5, 2019, the entireties of which are incorporated by reference herein.

BACKGROUND

Technical Field

The present invention relates to a method for culturing animal cells. An embodiment relates to a method for producing an objective substance, such as a protein, using animal cells.

Background Art

Animal cells have been used as expression hosts for recombinant proteins.

An example of such an expression host is the Chinese hamster ovary-derived cell line (CHO) reported in a method of feeding a feed medium containing phosphoric acid so that the concentration of phosphoric acid in a culture medium is 1.5 to 3.5 mM (Patent document 1).

In addition, methods for culturing cells have been reported using a culture medium containing a high concentration of choline (Patent document 2), a high concentration of serine (Patent document 3), or a high concentration of amine (Patent document 4).

PRIOR ART REFERENCES

Patent Documents

Patent document 1: U.S. Pat. No. 6,924,124
Patent document 2: WO2011/134921A1
Patent document 3: WO2008/136398A1
Patent document 4: WO2007/077217A2

SUMMARY

An aspect of the present invention is to provide a technique for improving the culture performance of animal cells, that is, the proliferation of animal cells and production of an objective substance by the animal cells.

It is described herein that the culture performance of animal cells, that is the proliferation of animal cells and production of an objective substance by animal cells, can be improved by enhancing the concentration of a specific component such as phosphoric acid and potassium in the culture medium when culturing the animal cells.

It is an aspect of the present invention to provide a method for producing an objective substance, the method comprising: culturing animal cells having an objective substance-producing ability in a culture medium; and collecting the objective substance, wherein the culturing is carried out under the following condition(s): (A) the phosphoric acid concentration in the culture medium is increased to be 4 mM or more; and/or (B) the potassium concentration in the culture medium is increased to be 1 mM or more.

It is a further aspect of the present invention to provide the method as described above, wherein the objective substance is a protein.

It is a further aspect of the present invention to provide the method for culturing animal cells, the method comprising: culturing the animal cells in a culture medium, wherein the culturing is carried out under the following condition(s): (A) the phosphoric acid concentration in the culture medium is increased to be 4 mM or more; and/or (B) the potassium concentration in the culture medium is increased to be 1 mM or more.

It is a further aspect of the present invention to provide the method as described above, wherein at least the phosphoric acid concentration in the culture medium is increased.

It is a further aspect of the present invention to provide the method as described above, wherein the phosphoric acid concentration in the culture medium during the culturing is 11 mM or more.

It is a further aspect of the present invention to provide the method as described above, wherein the phosphoric acid and/or potassium is present in the culture medium at said concentration at the start of the culturing.

It is a further aspect of the present invention to provide the method as described above, wherein the phosphoric acid and/or potassium is added to the culture medium after the start of the culturing so to be present in the culture medium at said concentration.

It is a further aspect of the present invention to provide the method as described above, wherein said concentration of the phosphoric acid and/or potassium in the culture medium is an average concentration over the whole period of the culturing.

It is a further aspect of the present invention to provide the method as described above, wherein the amount of the phosphoric acid is 0.05 mM or more per day over the whole period of the culturing.

It is a further aspect of the present invention to provide the method as described above, wherein the amount of the phosphoric acid is 0.5 mM or more per day over the whole period of the culturing.

It is a further aspect of the present invention to provide the method as described above, wherein the amount of the potassium is 0.2 mM or more per day over the whole period of the culturing.

It is a further aspect of the present invention to provide the method as described above, wherein the culturing is carried out by a perfusion culture using a feed medium having a phosphoric acid concentration of 4 mM or more.

It is a further aspect of the present invention to provide the method as described above, wherein the culturing is a perfusion culture using a feed medium having a phosphoric acid concentration of 11 mM or more.

It is a further aspect of the present invention to provide the method as described above, wherein the culturing is carried out in the presence of amine.

It is a further aspect of the present invention to provide the method as described above, wherein the amine is 1,4-butanediamine.

It is a further aspect of the present invention to provide the method as described above, wherein the culturing is carried out in the presence of choline and/or serine.

It is a further aspect of the present invention to provide the method as described above, wherein the amine concentration in the culture medium during the culturing is 0.002 mM or more.

It is a further aspect of the present invention to provide the method as described above, wherein the choline concentration in the culture medium during the culturing is 0.2 mM or more.

It is a further aspect of the present invention to provide the method as described above, wherein the serine concentration in the culture medium during the culturing is 2 mM or more.

It is a further aspect of the present invention to provide the method as described above, wherein the amine, choline, and/or serine is present in the culture medium at the start of the culturing.

It is a further aspect of the present invention to provide the method as described above, wherein the amine, choline, and/or serine is added to the culture medium after the start of the culturing so as to be present in the culture medium at said concentration.

It is a further aspect of the present invention to provide the method as described above, wherein said concentration of the amine, choline, and/or serine in the culture medium at said concentration is an average concentration over the whole period of the culturing.

It is a further aspect of the present invention to provide the method as described above, wherein the amount of the amine is 0.0005 mM or more per day over the whole period of the culturing.

It is a further aspect of the present invention to provide the method as described above, wherein the amount of choline is 0.05 mM or more per day over the whole period of the culturing.

It is a further aspect of the present invention to provide the method as described above, wherein the amount of the serine is 0.5 mM or more per day over the whole period of the culturing.

It is a further aspect of the present invention to provide a culture medium for culturing animal cells, wherein the phosphoric acid concentration and/or the potassium concentration in the culture medium is increased.

It is a further aspect of the present invention to provide the method as described above, wherein at least the phosphoric acid concentration is increased.

It is a further aspect of the present invention to provide the culture medium as described above, wherein the culture medium further contains amine.

It is a further aspect of the present invention to provide the culture medium as described above, wherein the amine is 1,4-butanediamine.

It is a further aspect of the present invention to provide the culture medium as described above, wherein the culture medium further contains choline and/or serine.

It is a further aspect of the present invention to provide the culture medium as described above, wherein the culture medium is a starting medium.

It is a further aspect of the present invention to provide the culture medium as described above, wherein the culture medium is a feed medium.

DETAILED DESCRIPTION OF THE EXEMPLARY EMBODIMENTS

<1> Method

Figure 1:
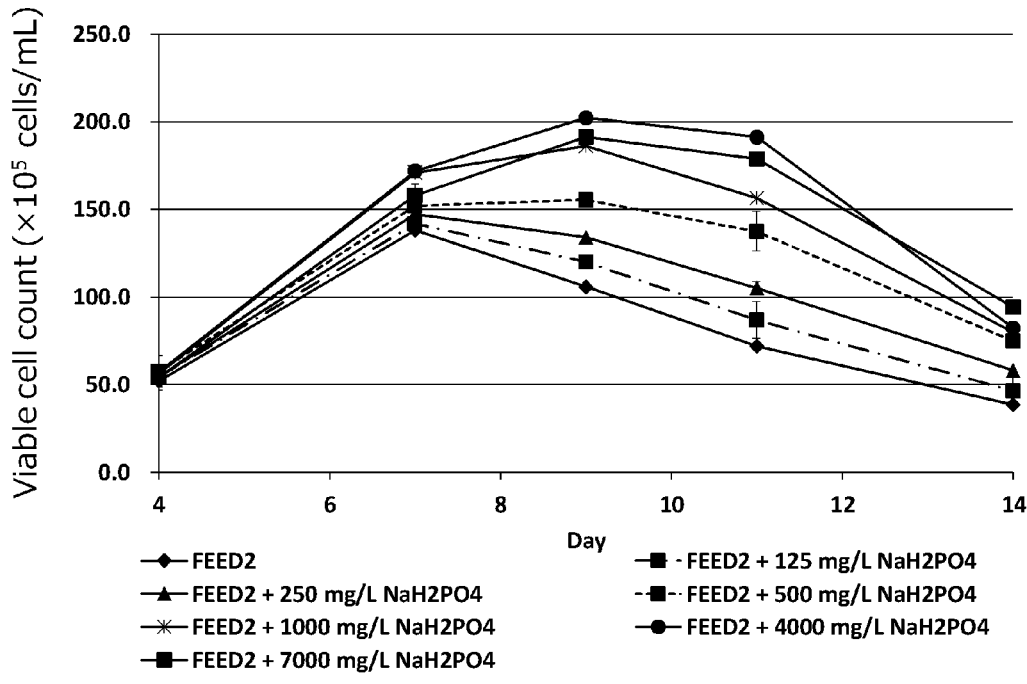
FIG. 1 depicts a diagram showing the effect of the concentration of phosphoric acid in a feed medium on proliferation of CHO cells.

The method as described herein is a method for culturing animal cells, which includes culturing the animal cells in a culture medium, wherein the culturing is carried out under conditions where the phosphoric acid concentration and/or the potassium concentration in the culture medium is increased.

In an embodiment, an objective substance may be produced by culturing the animal cells. That is, when the animal cells have an objective substance-producing ability, an objective substance can be produced by culturing the animal cells. That is, an embodiment of the method is a method for producing an objective substance, including a step of culturing animal cells having an objective substance-producing ability in a culture medium, and collecting the objective substance, wherein the culturing is carried out under conditions where the phosphoric acid concentration and/or the potassium concentration in the culture medium is increased.

The objective substance is not particularly limited, so long as it can be produced by animal cells. Examples of the objective substance include proteins. The protein to be produced as the objective substance is also referred to as "objective protein".

The animal cells are not particularly limited. The animal cells can be chosen according to various criteria such as the purpose of the animal cells. For example, when using the animal cells for production of the objective protein, the animal cells are not particularly limited, so long as they can express the objective protein. The animal cells can also be referred to as "host", "expression host", or "host cell". Examples of the animal from which the cells are derived include mammals, birds, and amphibians. Particular examples of the animal include mammals. Examples of the mammals include rodents and primates. Examples of the rodents include hamster, mouse, rat, and guinea pig. Examples of the hamster include Chinese hamster. Examples of the primates include human, monkey, and chimpanzee. Examples of the monkey include African green monkey. Examples of the birds include chicken. Examples of the amphibians include *Xenopus laevis*. The tissue or cell type from which the animal cells are derived is not particularly limited. Examples of the tissue or cell type from which the animal cells are derived include ovary, kidney, adrenal gland, tongue epithelium, olfactory epithelium, pineal body, thyroid gland, and melanocyte. Examples of the cells of Chinese hamster include Chinese hamster ovary-derived cell line (CHO). Specific examples of CHO include CHO-DG44 and CHO-K1. Examples of the cells of human include human embryonic kidney cell-derived cell line (HEK). Specific examples of HEK include HEK293 and HEK293T.

Examples of the cells of African green monkey include African green monkey kidney cell-derived cell line (COS). Specific examples of COS include COS-1. Specific examples of the cells of *Xenopus laevis* include *Xenopus laevis* oocyte.

The term "animal cells having an objective substance-producing ability" refers to animal cells having an ability to produce the objective substance. The term "animal cells having an objective substance-producing ability" may specifically refer to animal cells having an ability to, when being cultured in a culture medium, generate the objective substance, for example, express the objective protein, and accumulate the same in a culture broth to such an extent that the objective substance can be collected from the culture broth. The term "accumulation in a culture broth" may specifically refer to accumulation in a culture medium, on a cell surface layer, in cells, or in/on a combination thereof. Accumulation of the objective substance outside the cells, for example, in a culture medium or on a cell surface layer, is also referred to as "secretion" or "secretory production" of the objective substance. That is, the animal cells may have a secretory production ability of the objective substance, that is, an ability to produce the objective substance by secretory production. The accumulation amount of the objective substance may be, for example, 10 μg/L or more, 1 mg/L or more, 100 mg/L or more, or 1 g/L or more, in terms of the accumulation amount in a culture broth. The animal cells may be able to produce one kind of objective substance or two or more kinds of the objective sub stance.

The animal cells may inherently have an objective substance-producing ability, or may have been modified so as to have an objective substance-producing ability. The animal cells may also have been modified so that an objective substance-producing ability inherently possessed by them is increased. The animal cells having an objective substance-producing ability can be obtained by imparting an objective substance-producing ability to such animal cells as described above, or enhancing an objective substance-producing ability of such animal cells as described above. For example, an objective protein-producing ability can be imparted or increased by introduction of a gene encoding the objective protein. The gene encoding the objective protein is also referred to as "objective protein gene".

The objective protein is not particularly limited, so long as it can be expressed by using animal cells as a host. The objective protein may be a protein derived from or native to the host, or may be a heterologous protein. The term "heterologous protein" refers to an exogenous protein relative to the host producing that protein, that is, the animal cells having an objective protein-producing ability. The objective protein may be, for example, a naturally-present protein, a modified protein thereof, or a protein of which the amino acid sequence is artificially designed. The objective protein may be, for example, a protein derived from a microorganism, a protein derived from a plant, a protein derived from an animal, or a protein derived from a virus. The objective protein may particularly be a derived from human. The objective protein may be a monomeric protein or a multimeric protein. The objective protein may be a secretory protein or a non-secretory protein. The term "protein" also includes peptides, such as oligopeptides and polypeptides.

Specific examples of the objective protein include enzymes, physiologically active proteins, receptor proteins, antigenic proteins, and other proteins.

Examples of the enzymes include cellulase, transglutaminase, protein glutaminase, isomaltodextranase, protease, endopeptidase, exopeptidase, aminopeptidase, carboxypeptidase, collagenase, and chitinase.

Examples of the physiologically active proteins include growth factors, hormones, cytokines, and antibody-related molecules.

Examples of the growth factors include epidermal growth factor (EGF), insulin-like growth factor-1 (IGF-1), transforming growth factor (TGF), nerve growth factor (NGF), brain-derived neurotrophic factor (BDNF), vascular endothelial growth factor (VEGF), granulocyte-colony stimulating factor (G-CSF), granulocyte-macrophage-colony stimulating factor (GM-CSF), platelet-derived growth factor (PDGF), erythropoietin (EPO), thrombopoietin (TPO), acidic fibroblast growth factor (aFGF or FGF1), basic fibroblast growth factor (bFGF or FGF2), keratinocyte growth factor (KGF-1 or FGF7, and, KGF-2 or FGF10), hepatocyte growth factor (HGF), stem cell factor (SCF), and Activin. Examples of Activin include Activin A, C, and E.

Examples of the hormones include insulin, glucagon, somatostatin, human growth hormone (hGH), parathyroid hormone (PTH), calcitonin, and exenatide.

Examples of the cytokines include interleukins, interferons, and tumor necrosis factors (TNFs).

Furthermore, a physiologically active protein may be an intact protein, or may be a part of a protein. Examples of a part of a protein include, for example, a part having physiological activity. Specific examples of a part having physiological activity include, for example, Teriparatide, which is a physiologically active peptide having the N-terminal 34 amino acid residues of parathyroid hormone (PTH).

The term "antibody-related molecule" may refer to a protein having a single domain or a combination of two or more domains of a complete antibody. Examples of the domains of a complete antibody include heavy chain domains VH, CH1, CH2, and CH3, and light chain domains VL and CL. The antibody-related molecule may be a monomeric protein, or may be a multimeric protein, so long as it contains the above-mentioned domain(s). When the antibody-related molecule is a multimeric protein, it may be a homo-multimer having a single kind of subunit or may be a hetero-multimer having two or more kinds of subunits. Specific examples of the antibody-related molecules include a complete antibody, Fab, F(ab'), F(ab')$_2$, Fc, a dimer having a heavy chain (H chain) and a light chain (L chain), Fc-fusion protein, heavy chain (H chain), light chain (L chain), light chain Fv (scFv), sc(Fv)$_2$, disulfide-bonded Fv (sdFv), diabody, and VHH fragment (Nanobody (registered trademark)). More specific examples of the antibody-related molecules include Trastuzumab, Adalimumab, and Nivolumab.

Examples of the receptor proteins include receptor proteins for physiologically active proteins and other physiologically active substances. Examples of the other physiologically active substances include neurotransmitters such as dopamine. A receptor protein may be an orphan receptor of which the corresponding ligand is not known.

The antigen proteins are not particularly limited, so long as they can induce an immune response. An antigen protein can be appropriately selected depending on, for example, the intended object of the immune response. An antigen protein can be used as, for example, a vaccine.

Examples of other proteins include Liver-type fatty acid-binding protein (LFABP), fluorescent proteins, immunoglobulin-binding proteins, albumin, fibroin-like proteins, and extracellular proteins. Examples of the fluorescent proteins include Green Fluorescent Protein (GFP). Examples of the immunoglobulin-binding proteins include Protein A, Protein G, and Protein L. Examples of albumin include human serum albumin. Examples of the fibroin-like proteins include those disclosed in WO2017/090665 and WO2017/171001.

Examples of the extracellular protein include fibronectin, vitronectin, collagen, osteopontin, laminin, and partial sequences thereof. Laminin is a protein having a heterotrimeric structure having an α chain, a β chain, and a γ chain. Examples of laminin include laminin of mammals. Examples of the subunit chains of laminin (i.e. α, β, and γ chains) include 5 kinds of α chains (α1 to α5), 3 kinds of β chains (β1 to β3), and 3 kinds of γ chains (γ1 to γ3). Laminin constitutes various isoforms depending on combinations of these subunits. Specific examples of laminin include, for example, laminin 111, laminin 121, laminin 211, laminin 213, laminin 221, laminin 311, laminin 321, laminin 332, laminin 411, laminin 421, laminin 423, laminin 511, laminin 521, and laminin 523. Examples of the partial sequence of laminin include laminin E8, which is an E8 fragment of laminin. Laminin E8 is a protein having a heterotrimeric structure having an E8 fragment of α chain (α chain E8), an E8 fragment of β chain (β chain E8), and an E8 fragment of γ chain (γ chain E8). The subunit chains of laminin E8 (i.e. α chain E8, β chain E8, and γ chain E8) are also collectively referred to as "E8 subunit chains". Examples of the E8 subunit chains includes E8 fragments of the laminin subunit chains exemplified above. Laminin E8 constitutes various isoforms depending on combinations of these E8 subunit chains. Specific examples of laminin E8 include, for example, laminin 111E8, laminin 121E8, laminin 211E8, laminin 221E8, laminin 332E8, laminin 421E8, laminin 411E8, laminin 511E8, and laminin 521E8.

The objective protein may be, for example, a protein having any known or natural amino acid sequences of such proteins as described above. The objective protein may also be, for example, a variant of a protein having any known or natural amino acid sequences of such proteins as described above. Examples of the variant include a protein having any known or natural amino acid sequences including substitution, deletion, insertion, or addition of one or several amino acid residues at one or several positions. The number meant by the term "one or several" used above may specifically be, for example, 1 to 50, 1 to 40, 1 to 30, 1 to 20, 1 to 10, 1 to 5, or 1 to 3. Examples of the variant also include a protein having an amino acid sequence having an identity of, for example, 50% or more, 65% or more, 80% or more, 90% or more, 95% or more, 97% or more, or 99% or more, to the total amino acid sequence of any known or natural amino acid sequence. A protein specified with the type of organism from which the protein is derived is not limited to proteins per se found in that organism, and shall also include proteins having any of the amino acid sequences of proteins found in that organism and variants thereof. That is, for example, the term "protein derived from human" is not limited to proteins per se found in human, and shall also include proteins having any of the amino acid sequences of proteins found in human and variants thereof.

The term "identity" between amino acid sequences means an identity between the amino acid sequences calculated by blastp with default scoring parameters (i.e. Matrix, BLOSUM62; Gap Costs, Existence=11, Extension=1; Compositional Adjustments, Conditional compositional score matrix adjustment), unless otherwise stated.

The objective protein gene is not particularly limited, so long as it encodes such an objective protein as described above. The objective protein gene may be, for example, a gene having any known or natural nucleotide sequences of genes encoding such proteins as described above. The objective protein gene may also be, for example, a variant of a gene having any known or natural nucleotide sequences of genes encoding such proteins as described above. The objective protein gene may have been modified, for example, to encode a protein having such a variant sequence as exemplified above. In the objective protein gene, any codon(s) may be replaced with respective equivalent codon(s) thereof. For example, the objective protein gene may have been modified to have optimal codons according to the codon usage frequency of the host cell.

The term "gene" is not limited to DNA, but may include any polynucleotide, so long as it encodes a corresponding expression product. That is, the term "objective protein gene" may mean any polynucleotide encoding the objective protein. The objective protein gene may be DNA, RNA, or a combination thereof. The objective protein gene may be single-stranded or double-stranded. The objective protein gene may be single-stranded DNA or single-stranded RNA. The objective protein gene may be double-stranded DNA, double-stranded RNA, or a hybrid strand having a DNA strand and an RNA strand. The objective protein gene may contain both a DNA residue and an RNA residue in a single polynucleotide chain. The objective protein gene may or may not contain an intron. The embodiment of the objective protein gene can be appropriately chosen according to various conditions such as means for expressing the objective protein.

The expression "having a (nucleotide or amino acid) sequence" means "including the (nucleotide or amino acid) sequence" unless otherwise stated, and also can mean "having only the (nucleotide or amino acid) sequence".

The objective protein is expressed from the objective protein gene. That is, the animal cells having an objective protein-producing ability have the objective protein gene. Specifically, the animal cells having an objective protein-producing ability have the objective protein gene so that the gene can be expressed. Incidentally, it is sufficient that the animal cells having an objective protein-producing ability have the objective protein gene until the objective protein is expressed to a desired extent. That is, the animal cells having an objective protein-producing ability may or may not have the objective protein gene after expression of the objective protein. The terms "expression of the objective protein gene" and "expression of the objective protein" may be used synonymously with each other.

The objective protein gene can be obtained by cloning from an organism having the objective protein gene. For cloning, for example, nucleotides containing the gene, such as genomic DNA and cDNA, can be used. The objective protein gene can also be obtained by chemical synthesis (Gene, 60(1), 115-127 (1987)).

The obtained objective protein gene can be used as it is, or after being modified as required. That is, the objective protein gene can be modified to obtain a variant thereof. A gene can be modified by a known technique. For example, an objective mutation can be introduced into an objective site of DNA by the site-specific mutation method. Examples of the site-specific mutation method include the method utilizing PCR (Higuchi, R., 61, in PCR Technology, Erlich, H. A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a variant of the objective protein gene may also be obtained directly by chemical synthesis.

Modes of introducing the objective protein gene into the host cell are not particularly limited. It is sufficient that the objective protein gene is harbored by the host cell in such a manner that it can be expressed. Specifically, for example, in cases of introducing the objective protein gene in the form requiring transcription, such as DNA, it is sufficient that the objective protein gene is harbored by the host cell in such a manner that it can be expressed under control of a promoter that functions in the host cell. In the host cell, the objective protein gene may be present outside the chromosome, or may have been integrated into the chromosome. In cases of introducing two or more genes, it is sufficient that the genes are harbored by the host cell in such a manner that they each can be expressed.

The promoter for expressing the objective protein gene is not particularly limited so long as it functions in the host cell. The term "promoter that functions in host cell" refers to a promoter that has a promoter activity in the host cell. The promoter may be a promoter derived from or native to the host cell, or a heterogenous promoter. The promoter may be the native promoter of the objective protein gene, or a promoter of another gene. The promoter may also be stronger than the native promoter of the objective protein gene. Examples of promoters that function in animal cells include SV40 promoter, EF1a promoter, RSV promoter, CMV promoter, and SRalpha promoter. As the promoter, a highly-active type of an existing promoter may also be obtained and used by using various reporter genes. Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The objective protein gene can be introduced into the host cell by, for example, using a vector containing the gene. The vector containing the objective protein gene is also referred to as "expression vector for the objective protein gene". The expression vector for the objective protein gene can be constructed by, for example, ligating a DNA fragment containing the objective protein gene with a vector. By introducing the expression vector for the objective protein gene into the host cell, the gene can be introduced into the host cell. The vector may contain a marker such as a drug resistance gene. Furthermore, the vector may contain an expression control sequence, such as a promoter, for expressing the inserted gene. The vector can be appropriately selected according to various conditions such as the type of the host cell and the mode of introducing the objective protein gene. Examples of vectors usable for gene introduction into animal cells include plasmid vectors and viral vectors. Examples of the viral vectors include, for example, retroviral vectors and adenoviral vectors. Examples of the plasmid vectors include, for example, pcDNA series vectors (e.g. pcDNA3.1; Thermo Fisher Scientific), pBApo-CMV series vectors (TAKARA BIO), and pCI-neo (Promega). Depending on the type and structure of the vector, the vector can be integrated into the chromosome of the host cell, autonomously replicated outside the chromosome of the host cell, or temporarily held outside the chromosome of the host cell. For example, a vector having a viral replication origin, such as SV40 replication origin, can be autonomously replicated outside the chromosome in animal cells. Specifically, for example, the pcDNA series vectors have the SV40 replication origin, and hence can be autonomously replicated outside the chromosome in the host cell expressing the SV40 large T antigen, such as COS-1 and HEK293T.

Alternatively, the objective protein gene can be introduced into the host cell by, for example, introducing a nucleotide fragment containing the gene into the host cell. Examples of such a nucleotide fragment include linear DNA and linear RNA. Examples of the linear RNA include, for example, mRNA and cRNA.

Methods for introducing a nucleotide such as a vector and nucleotide fragment into the host cell can be appropriately selected according to various conditions such as the type of the host cell. Examples of methods for introducing a nucleotide such as a vector and nucleotide fragment into animal cells include DEAE dextran, calcium phosphate, lipofection, electroporation, and microinjection. When the vector is a viral vector, the vector can be introduced into the host cell by infecting the host cell with the vector (virus).

Furthermore, cells inherently having the objective protein gene may be modified so that the expression of the objective protein gene is increased, and then used. The expression "the expression of a gene is increased" means that the expression amount of the gene per cell is increased as compared with that of a non-modified cell. The term "non-modified cell" used herein refers to a control cell that has not been modified so that the expression of an objective gene is increased. Examples of the non-modified cell include a wild-type cell and a cell from which the host cell is obtained though modification. Examples of methods for increasing the expression of the objective protein gene include increasing the copy number of the objective protein gene and improving the transcription efficiency and/or translation efficiency of the objective protein gene. The copy number of the objective protein gene can be increased by introducing the objective protein gene into the host cell. Introduction of the objective protein gene can be carried out as described above. The objective protein gene to be introduced may be one derived from the host cell, or a heterogenous one. The transcription efficiency and/or translation efficiency of the objective protein gene can be improved by modifying an expression control sequence of the gene, such as a promoter. For example, the transcription efficiency of the objective protein gene can be improved by replacing the promoter of the objective protein gene with a stronger promoter.

The culture of the animal cells is carried out under conditions where the phosphoric acid concentration and/or the potassium concentration in the culture medium is increased. The culture of the animal cells may be carried out under conditions where at least the phosphoric acid concentration in the culture medium is increased. The "conditions where the phosphoric acid concentration and/or the potassium concentration in the culture medium is increased" are also referred to as "phosphate/potassium-increased conditions". The "conditions where the phosphoric acid concentration in the culture medium is increased" are also particularly referred to as "phosphate-increased conditions". The "conditions where the potassium concentration in the culture medium is increased" are also particularly referred to as "potassium-increased conditions". The "conditions where none of the phosphoric acid concentration and the potassium concentration in the culture medium is increased" are also referred to as "control conditions". Examples of the control conditions include usual conditions used for culture of animal cells. Specific examples of the control conditions include conditions not satisfying the phosphate/potassium-increased conditions exemplified below.

By culturing the animal cells under the phosphate/potassium-increased conditions, the culture performance of the animal cells can be improved. Specifically, by culturing the animal cells under the phosphate/potassium-increased conditions, the culture performance of the animal cells can be improved as compared with a case of culturing the animal cells under the control conditions. Furthermore, for example, by culturing the animal cells under conditions where both of the phosphoric acid concentration and the potassium concentration in the culture medium are increased, the culture performance of the animal cells may be improved as compared with a case of culturing the animal cells under conditions where either one of the phosphoric acid concentration and the potassium concentration in the culture medium is increased. Examples of the improvement of the culture performance of the animal cells include improvement of the proliferation of the animal cells, improvement of the survival rate of the animal cells, improvement of production of the objective substance by the animal cells, and elongation of the culture period of the animal cells.

That is, by culturing the animal cells under the phosphate/potassium-increased conditions, for example, the proliferation and/or survival rate of the animal cells may be improved. Specifically, by culturing the animal cells under the phosphate/potassium-increased conditions, the proliferation and/or survival rate of the animal cells may be improved as compared with a case of culturing the animal cells under the control conditions. By culturing the animal cells under the phosphate/potassium-increased conditions, the viable cell density of the animal cells may reach, during the culture, for example, a density of 1.5 times or more, 2 times or more, 2.5 times or more, 3 times or more, 3.5 times or more, 4 times or more, 5 times or more, 7 times or more, 10 times or more, 20 times or more, 30 times or more, 40 times or more, 50 times or more, 60 times or more, 70 times or more, 80 times or more, 90 times or more, 100 times or more, 200 times or more, 500 times or more, or 1000 times or more the viable cell density at the star of the culture. By culturing the animal cells under the phosphate/potassium-increased conditions, the viable cell density of the animal cells may reach, during the culture, for example, a density of $1.5 \times 10^7$ cells/mL or more, $1.6 \times 10^7$ cells/mL or more, $1.7 \times 10^7$ cells/mL or more, $1.8 \times 10^7$ cells/mL or more, $1.9 \times 10^7$ cells/mL or more, $2 \times 10^7$ cells/mL or more, $3 \times 10^7$ cells/mL or more, $5 \times 10^7$ cells/mL or more, $7 \times 10^7$ cells/mL or more, $1 \times 10^8$ cells/mL or more, or $1 \times 10^9$ cells/mL or more. The viable cell count of the animal cells can be measured by, for example, using a viable/dead cells autoanalyzer Vi-CELL™ XR (Beckman Coulter) or a flow cytometer guava easyCyte (Luminex).

Furthermore, when the animal cells have an objective substance-producing ability such as an objective protein-producing ability, by culturing the animal cells under the phosphate/potassium-increased conditions, for example, production of the objective substance such as the objective protein by the animal cells may be improved. Specifically, when the animal cells have an objective substance-producing ability such as an objective protein-producing ability, by culturing the animal cells under the phosphate/potassium-increased conditions, production of the objective substance such as the objective protein by the animal cells may be improved as compared with a case of culturing the animal cells under the control conditions.

Furthermore, by culturing the animal cells under the phosphate/potassium-increased conditions, for example, the culture period of the animal cells may be elongated. Specifically, by culturing the animal cells under the phosphate/potassium-increased conditions, the culture period of the animal cells may be elongated as compared with a case of culturing the animal cells under the control conditions. Examples of the elongation of the culture period of the animal cells include elongation of a period where the proliferation of the animal cells continues, elongation of a period where the animal cells are maintained (i.e. the animal cells survive), and elongation of a period where production of the objective substance such as the objective protein by the animal cells continues.

In other words, an embodiment of the method as described herein may be a method for improving the proliferation of the animal cells. An embodiment of the method may also be a method for improving the survival rate of the animal cells. An embodiment of the method may also be a method for improving production of the objective substance by the animal cells. An embodiment of the method may also be a method for elongating the culture period of the animal cells.

The term "culture of animal cells" is not limited to culture for the purpose of the proliferation of the animal cells, but may also include culture not for the purpose of the proliferation of the animal cells, such as culture for the purpose of maintenance of the animal cells and production of the objective substance by the animal cells.

The culture medium composition and culture conditions are not particularly limited, except that the phosphoric acid concentration and/or the potassium concentration in the culture medium is/are increased, so long as the purpose for the culture of the animal cells can be attained. For example, when the culture is carried out for the purpose of the proliferation of the animal cells, the culture medium composition and culture conditions can be configured so that the animal cells proliferate. Furthermore, for example, when the culture is carried out for the purpose of maintenance of the animal cells, the culture medium composition and culture conditions can be configured so that the animal cells are maintained (i.e. the animal cells survive). Furthermore, for example, when the culture is carried out for the purpose of production of the objective substance such as the objective protein by the animal cells, the culture medium composition and culture conditions can be configured so that the objective substance is produced (e.g. the objective protein is expressed). When the culture is carried out not for the purpose of the proliferation of the animal cells, the animal cells may or may not proliferate during the culture. Even when the culture is carried out not for the purpose of the proliferation of the animal cells, the animal cells may typically proliferate during the culture. The culture medium composition and culture conditions can be set according to various conditions such as the type of the animal cells. The culture can be carried out by, for example, using a usual culture medium and usual conditions used for culture of animal cells as they are, or after modifying them as required, except that the phosphoric acid concentration and/or the potassium concentration in the culture medium is increased.

The culture can be carried out by, for example, using a liquid culture medium. Specific examples of the culture medium usable for culture of animal cells include D-MEM (Dulbecco's Modified Eagle Medium), CELLiST Basal Media BASAL4P (Ajinomoto), Opti-MEM (Thermo Fisher Scientific), RPMI 1640 (Thermo Fisher Scientific), CD293 (Thermo Fisher Scientific), CHO-S-SFMII (Thermo Fisher Scientific), CHO-SF (Sigma-Aldrich), EX-CELL CD CHO (Sigma-Aldrich), EX-CELL™ 302 (Sigma-Aldrich), IS CHO-CD (Irvine Scientific), and IS CHO-CDXP (Irvine Scientific). The culture medium may contain various culture medium components such as carbon sources, amino acids, vitamins, inorganic salts, phosphate, choline, amines, pH buffers, growth factors, serum, serum albumin, selective agents, and gene expression inducers. Examples of the carbon sources include glucose. Examples of the amino acids include 20 amino acids constituting proteins and derivatives thereof. The amino acids each may be, for example, an L-isomer. Specific examples of the amino acids include glutamine and serine. Examples of glutamine include L-glutamine. Examples of serine include L-serine. Examples of the amines include 1,4-butanediamine (also called "putrescine"), agmatine, methylamine, dimethylamine, trimethylamine, ethylamine, diethylamine, triethylamine, ethylenediamine, ethanolamine, diethanolamine, triethanolamine, N,N-diisopropylethylamine, tetramethylethylenediamine, hexamethylenediamine, spermidine, spermine, and amantadine. Examples of aromatic amines include aniline, phenethylamine, toluidine, catecholamine, and 1,8-bis(dimethylamino)naphthalene. Examples of heterocyclic amines include pyrrolidine, piperidine, piperazine, morpholine, quinuclidine, 1,4-diazabicyclo[2.2.2]octane, pyrrole, pyrazole, imidazole, pyridine, pyridazine, pyrimidine, pyrazine, oxazole, thiazole, and 4-dimethylaminopyridine. Particular examples of the amines include 1,4-butanediamine, ethanolamine, spermidine, and spermine. More particular examples of the amines include 1,4-butanediamine.

Components that can form a salt each may be used as a free compound, a salt thereof, or a combination of them. That is, for example, the term "amino acid" may mean an amino acid in the form of free compound, a salt thereof, or a combination of them, unless otherwise stated. Also, for example, the term "phosphoric acid" may mean phosphoric acid in the form of free compound, a salt thereof, or a combination of them, unless otherwise stated. Also, for example, the term "choline" may mean choline in the form of free compound, a salt thereof, or a combination of them, unless otherwise stated. Also, for example, the term "amine" may mean amine in the form of free compound, a salt thereof, or a combination of them, unless otherwise stated. The salt is not particularly limited, so long as it is usable for culture of animal cells. For example, examples of salts for acidic groups such as phosphate group and carboxyl group include ammonium salts, salts with alkali metals such as sodium and potassium, salts with alkaline earth metals such as calcium and magnesium, aluminum salts, zinc salts, salts with such amines as exemplified above, and salts with basic amino acids such as arginine and lysine. Also, for example, examples of salts for basic groups such as amino group include salts with inorganic acids such as hydrochloric acid, sulfuric acid, phosphoric acid, nitric acid, and hydrobromic acid, salts with organic carboxylic acids such as acetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, and malic acid, and salts with organic sulfonic acid such as methanesulfonic acid, benzenesulfonic acid, and p-toluenesulfonic acid. Specifically, for example, particular examples of the salt of phosphoric acid include sodium dihydrogen phosphate, disodium hydrogen phosphate, potassium dihydrogen phosphate, and dipotassium hydrogen phosphate. Specifically, for example, particular examples of the salt of choline include choline bitartrate.

The inoculation amount of the animal cells at the start of the culture, for example, may be $1 \times 10^3$ cells/mL or more, $1 \times 10^4$ cells/mL or more, $1 \times 10^5$ cells/mL or more, $1 \times 10^6$ cells/mL or more, or $1 \times 10^7$ cells/mL; or may be $1 \times 10^{10}$ cells/mL or less, $1 \times 10^9$ cells/mL or less, $1 \times 10^8$ cells/mL or less, $1 \times 10^7$ cells/mL or less, $1 \times 10^6$ cells/mL or less, $1 \times 10^5$ cells/mL or less, or $1 \times 10^4$ cells/mL or less.

The culture may also be carried out separately as seed culture and main culture. The culture conditions of the seed culture and the culture conditions of the main culture may be or may not be the same. When the culture is carried out for the purpose of production of the objective substance such as the objective protein, it is sufficient that the objective substance is produced at least during the main culture. For example, the animal cells may be allowed to sufficiently proliferate by seed culture, and then the objective substance such as the objective protein may be produced.

The culture can be carried out as batch culture, fed-batch culture, continuous culture, or a combination of these. Examples of the fed-batch culture or the continuous culture include a perfusion culture. The culture medium used at the start of the culture is also referred to as "starting medium" or "basal medium". The culture medium supplied to the culture system (e.g. starting medium) in the fed-batch culture or the continuous culture is also referred to as "feed medium". To add a feed medium to the culture system in the fed-batch culture or the continuous culture is also referred to as "feed". The feeding may be carried out over the whole period of the culture, or may be carried out during only a partial period of the culture. The feeding may be carried out continuously, or may be carried out intermittently. Upon the culture, in particular, fed-batch culture or continuous culture, such as perfusion culture, discharge of the culture broth may be carried out. The discharge of the culture broth may be, for example, discharge of a culture broth containing animal cells or discharge of a culture supernatant. Furthermore, animal cells may be collected from the discharged culture broth and may be returned to the culture system. The discharge of the culture broth may be carried out over the whole period of the culture or may be carried out during only a partial period of the culture. The discharge of the culture broth may be carried out continuously or may be carried out intermittently. The discharge of the culture broth and the feeding may be or may not be carried out simultaneously. It is preferred that the volume of the culture broth to be discharged is an equal volume to the volume of the feed medium to be fed. The term "equal volume" may mean an amount of 93 to 107% (v/v) to the volume of the feed medium to be fed. Furthermore, when the culture is carried out separately as seed culture and main culture, the culture schemes of the seed culture and the main culture may be or may not be the same.

The various components such as phosphoric acid may be contained in the starting medium, the feed medium, or both. That is, the various components such as phosphoric acid may be added to the culture medium independently or in any combination during the culture. These components may be added once or a plurality of times, or may be continuously supplied. The compositions, e.g. the types and/or concentrations of contained components, of the starting medium and the feed medium may be or may not be the same. That is, the types of the components present in the starting medium may be or may not be the same as those of the components present in the feed medium. Furthermore, the concentrations of the components contained in the starting medium may be or may not be the same as the concentrations of the components present in the feed medium. The compositions of the starting medium and the feed medium may be the same, for example, when the feed medium is used for perfusion culture. Furthermore, two or more kinds of feed media having different compositions, e.g. containing components of different types and/or different concentrations, may be used. For example, when the feeding is intermittently carried out two or more times, the composition of the feed medium may be or may not be the same for each feeding. Furthermore, the various components such as phosphoric acid may be added to the culture medium separate from the feed medium, e.g. in the form of powder.

The culture may be carried out, for example, under a $CO_2$-containing atmosphere, such as 5% $CO_2$. The pH of the culture medium may be, for example, around neutral. The term "around neutral" may refer to, for example, pH 6 to 8, pH 6.5 to 7.5, or pH 6.8 to 7.2. The pH of the culture medium can be adjusted during the culture as required. The pH of the culture medium can be adjusted by using various alkaline or acidic substances such as ammonia gas, aqueous ammonia, sodium carbonate, sodium bicarbonate, potassium carbonate, potassium bicarbonate, magnesium carbonate, sodium hydroxide, potassium hydroxide, calcium hydroxide, and magnesium hydroxide. The culture temperature may be, for example, 36 to 38° C. The culture period, for example, may be 0.5 day or longer, 1 day or longer, 2 days or longer, 3 days or longer, 4 days or longer, 5 days or longer, 6 days or longer, 7 days or longer, 8 days or longer, 9 days or longer, 10 days or longer, 12 days or longer, 15 days or longer, or 20 days or longer; and may be 50 days or shorter, 40 days or shorter, 30 days or shorter, 25 days or shorter, 20 days or shorter, 15 days or shorter, 12 days or shorter, 10 days or shorter, 9 days or shorter, 8 days or shorter, or 7 days or shorter, or may be within a range defined as a non-contradictory combination thereof. The culture period may be, specifically, for example, 1 to 30 days, 3 to 25 days, or 5 to 20 days. Expression of a gene such as the objective protein gene may be induced as required upon the culture.

The various components such as phosphoric acid each may be present in any form in the culture medium. For example, when a certain component is a component that can be ionized, the certain component may be or may not be ionized in the culture medium.

The term "the concentration of a certain component" when the certain component can be present in multiple forms in a liquid may refer to the total concentration of the certain component dissolved therein. That is, for example, the term "the concentration of a certain component" when the certain component can be present in the forms of molecule and ion in a liquid may refer to the sum of the concentration of molecule and the concentration of ion of the certain component. For example, the term "the concentration of a certain component in a culture medium" when the certain component can be present in multiple forms in the culture medium may refer to the total concentration of the certain component dissolved in the culture medium. That is, for example, the term "the concentration of a certain component in a culture medium" when the certain component can be present in the forms of molecule and ion in the culture medium may refer to the sum of the concentration of molecule and the concentration of ion of the certain component in the culture medium.

For example, the term "phosphoric acid concentration" may refer to the total concentration of dissolved phosphoric acid species. That is, for example, the term "phosphoric acid concentration" may specifically refer to the sum of the concentration of phosphoric acid molecule ($H_3PO_4$) and the concentration of phosphoric acid ion ($PO_4^{3-}$, $HPO_4^{2-}$, and $H_2PO_4^-$). For example, the term "phosphoric acid concentration in a culture medium" may refer to the total concentration of phosphoric acid species dissolved in the culture medium. That is, for example, the term "phosphoric acid concentration in a culture medium" may specifically refer to the sum of the concentration of phosphoric acid molecule ($H_3PO_4$) in the culture medium and the concentration of phosphoric acid ion ($PO_4^{3-}$, $HPO_4^{2-}$, and $H_2PO_4^-$) in the culture medium.

The increased amount of the phosphoric acid concentration and/or the potassium concentration in the culture medium is not particularly limited, so long as the culture performance of the animal cells, e.g. proliferation of the animal cells and production of the objective substance by the animal cells, is improved. The increased amount of the phosphoric acid concentration and/or the potassium concentration in the culture medium can be set according to various conditions such as the type of the animal cells, the length of the culture period, and a desired production amount of the objective substance.

The phrase "culture is carried out under conditions where the phosphoric acid concentration and/or the potassium concentration in a culture medium is increased" may mean, for example, that the phosphoric acid concentration and/or the potassium concentration in the culture medium is within a given range.

The phosphoric acid concentration in the culture medium, for example, may be 0.2 mM or more, 0.5 mM or more, 1 mM or more, 1.5 mM or more, 2 mM or more, 2.5 mM or more, 3 mM or more, 3.5 mM or more, 4 mM or more, 4.5 mM or more, 5 mM or more, 5.5 mM or more, 6 mM or more, 6.5 mM or more, 7 mM or more, 7.5 mM or more, 8 mM or more, 8.5 mM or more, 9 mM or more, 9.5 mM or more, 10 mM or more, 11 mM or more, 12 mM or more, 13 mM or more, 14 mM or more, 15 mM or more, 16 mM or more, 17 mM or more, 18 mM or more, 19 mM or more, or 20 mM or more and may be 100 mM or less, 70 mM or less, 50 mM or less, 40 mM or less, 30 mM or less, 29 mM or less, 28 mM or less, 27 mM or less, 26 mM or less, 25 mM or less, 24 mM or less, 23 mM or less, 22 mM or less, 21 mM or less, 20 mM or less, 19 mM or less, 18 mM or less, 17 mM or less, 16 mM or less, 15 mM or less, 14 mM or less, 13 mM or less, 12 mM or less, 11 mM or less, 10 mM or less, 9 mM or less, 8 mM or less, 7 mM or less, 6 mM or less, or 5 mM or less, or may be within a range defined as a non-contradictory combination thereof. The phosphoric acid concentration in the culture medium may be, in particular, 4 mM or more. The phosphoric acid concentration in the culture medium may be, in more particular, 11 mM or more. The phosphoric acid concentration in the culture medium may be, specifically, for example, 0.2 to 100 mM, 4 to 70 mM, 11 to 50 mM, 11 to 40 mM, 11 to 30 mM, 11 to 27 mM, or 10 to 25 mM.

The potassium concentration in the culture medium, for example, may be 0.2 mM or more, 0.5 mM or more, 1 mM or more, 2 mM or more, 3 mM or more, 4 mM or more, 5 mM or more, 6 mM or more, 7 mM or more, 8 mM or more, 9 mM or more, or 10 mM or more; and may be 50 mM or less, 40 mM or less, 30 mM or less, 20 mM or less, 15 mM or less, 12 mM or less, 10 mM or less, 9 mM or less, 8 mM or less, 7 mM or less, 6 mM or less, or 5 mM or less, or may be within a range defined as a non-contradictory combination thereof. The potassium concentration in the culture medium may be, in particular, 1 mM or more. The potassium concentration in the culture medium may be, specifically, for example, 0.2 to 50 mM, 0.5 to 30 mM, or 1 to 10 mM.

The phosphoric acid concentration and/or the potassium concentration in the culture medium may be increased over the whole period of the culture, or may be increased during only a partial period of the culture. That is, it is sufficient that the phrase "culture is carried out under conditions where the phosphoric acid concentration and/or the potassium concentration in a culture medium is increased" means that the phosphoric acid concentration and/or the potassium concentration in the culture medium is increased during at least a partial period of the culture, and the phrase does not necessary mean that the phosphoric acid concentration and/or the potassium concentration in the culture medium is increased over the whole period of the culture.

The phosphoric acid concentration and/or the potassium concentration in the culture medium, for example, may be increased to the concentration exemplified above over the whole period of the culture, or may be increased to the concentration exemplified above during only a partial period of the culture. That is, it is sufficient that the phrase "culture is carried out under conditions where the phosphoric acid concentration and/or the potassium concentration in a culture medium is increased to a certain concentration" or the phrase "culture is carried out in a culture medium having a certain phosphoric acid concentration and/or a certain potassium concentration" means that the phosphoric acid concentration and/or the potassium concentration in the culture medium is within the range of the certain concentration during at least a partial period of the culture, and the phrase does not necessarily mean that the phosphoric acid concentration and/or the potassium concentration in the culture medium is within the range of the certain concentration over the whole period of the culture. For example, phosphoric acid and/or potassium may be present in the culture medium at the concentration exemplified above at the start of the culture, or may be added to the culture medium to provide the concentration exemplified above after the start of the culture. Also, for example, phosphoric acid and/or potassium may be present in the culture medium at the concentration exemplified above at the start of the culture, and may be further added to the culture medium to the concentration exemplified above after the start of the culture (e.g. after consumption). In cases where the culture is carried out separately as seed culture and main culture, it is sufficient that the phosphoric acid concentration and/or the potassium concentration in the culture medium is increased at least during the main culture, i.e. over the whole period of the main culture or during a partial period of the main culture. That is, the phosphoric acid concentration and/or the potassium concentration in the culture medium may be or may not be increased during the seed culture. In such cases, terms regarding the culture, such as "culture period (period of culture)" and "start of culture", can be read as those regarding the main culture.

The "partial period" is not particularly limited, so long as the culture performance of the animal cells, e.g. proliferation of the animal cells and production of the objective substance by the animal cells, is improved. The "partial period" can be set according to various conditions such as the type of the animal cells, the length of the culture period, and a desired production amount of the objective substance. The "partial period" may be, for example, a period having a length of 50% or longer, 60% or longer, 70% or longer, 80% or longer, 90% or longer, 95% or longer, 97% or longer, or 99% or longer of the whole period of the culture. The "partial period" may also be, for example, a period having a length of 0.5 day or longer, 1 day or longer, 2 days or longer, 3 days or longer, 4 days or longer, 5 days or longer, 6 days or longer, 7 days or longer, 8 days or longer, 9 days or longer, 10 days or longer, 12 days or longer, or 15 days or longer.

The phosphoric acid concentration and/or the potassium concentration in the culture medium may also be increased to the concentration exemplified above, for example, in terms of the average concentration over the whole period of the culture. That is, the phrase "culture is carried out under conditions where the phosphoric acid concentration and/or the potassium concentration in a culture medium is increased to be a certain concentration" or the phrase "culture is carried out in a culture medium having a certain phosphoric acid concentration and/or a certain potassium concentration" may also mean that the phosphoric acid concentration and/or the potassium concentration in the culture medium in terms of the average concentration over the whole period of the culture is within the range of the certain concentration. The term "the phosphoric acid concentration and/or the potassium concentration in the culture medium in terms of the average concentration over the whole period of the culture" is not particularly limited so long as the transition of the phosphoric acid concentration and/or the potassium concentration in the culture medium over the whole period of the culture can be recognized, and may refer to, for example, the average of the phosphoric acid concentrations and/or the average of the potassium concentrations in the culture medium measured every 60 minutes, every 30 minutes, every 20 minutes, or every 10 minutes.

The phrase "culture is carried out under conditions where the phosphoric acid concentration and/or the potassium concentration in a culture medium is increased" may also mean, for example, that the amount of phosphoric acid and/or potassium added to the culture medium is within a given range.

The amount of phosphoric acid added to the culture medium, for example, may be 0.05 mM or more, 0.1 mM or more, 0.15 mM or more, 0.2 mM or more, 0.25 mM or more, 0.3 mM or more, 0.35 mM or more, 0.4 mM or more, 0.45 mM or more, 0.5 mM or more, 0.55 mM or more, 0.6 mM or more, 0.65 mM or more, 0.7 mM or more, 0.75 mM or more, 0.8 mM or more, 0.85 mM or more, 0.9 mM or more, 0.95 mM or more, or 1 mM or more; and may be 5 mM or less, 4 mM or less, 3 mM or less, 2 mM or less, or 1 mM or less, or may be within a range defined as a non-contradictory combination thereof, per day over the whole period of the culture. The amount of phosphoric acid added to the culture medium may be, in particular, 0.05 mM or more per day over the whole period of the culture. The amount of phosphoric acid added to the culture medium may be, in particular, 0.5 mM or more per day over the whole period of the culture. The amount of phosphoric acid added to the culture medium may be, specifically, for example, 0.05 to 5 mM, 0.1 to 4 mM, 0.4 to 3 mM, or 0.7 to 2 mM per day over the whole period of the culture.

The amount of potassium added to the culture medium, for example, may be 0.05 mM or more, 0.1 mM or more, 0.15 mM or more, 0.2 mM or more, 0.25 mM or more, 0.3 mM or more, 0.35 mM or more, 0.4 mM or more, 0.45 mM or more, or 0.5 mM or more; and may be 5 mM or less, 4.5 mM or less, 4 mM or less, 3.5 mM or less, 3 mM or less, 2.5 mM or less, 2 mM or less, 1.5 mM or less, 1 mM or less, 0.7 mM or less, 0.5 mM or less, or 0.2 mM or less, or may be within a range defined as a non-contradictory combination thereof, per day over the whole period of the culture. The amount of potassium added to the culture medium may be, in particular, 0.2 mM or more per day over the whole period of the culture. The amount of potassium added to the culture medium may be, specifically, for example, 0.05 to 5 mM, 0.1 to 3 mM, or 0.2 to 1 mM per day over the whole period of the culture.

Phosphoric acid and/or potassium may be added to the culture medium, for example, continuously or intermittently. Phosphoric acid and/or potassium may be added to the culture medium, for example, every day or every few days.

Phosphoric acid and/or potassium may be added to the culture medium at a time when the viable cell density of the animal cells is a density of $1.5\times10^6$ cell/mL or more, $1.6\times10^6$ cell/mL or more, $1.7\times10^6$ cell/mL or more, $1.8\times10^6$ cell/mL or more, $1.9\times10^6$ cell/mL or more, $2\times10^6$ cell/mL or more, $3\times10^6$ cell/mL or more, $5\times10^6$ cell/mL or more, $7\times10^6$ cell/mL or more, $1\times10^7$ cell/mL or more, or $1\times10^8$ cell/mL or more.

The culture may be carried out in the presence of amine, choline, and/or serine. The culture may be carried out in the presence of amine, choline, and/or serine, for example, when at least the phosphoric acid concentration in the culture medium is increased. The culture may be carried out, for example, at least in the presence of amine. The culture may be carried out, for example, at least in the presence of choline and/or serine.

The phrase "culture is carried out in the presence of amine, choline, and/or serine" may mean, for example, that the culture medium contains amine, choline, and/or serine.

The amine concentration in the culture medium, for example, may be 0.001 mM or more, 0.002 mM or more, 0.005 mM or more, 0.01 mM or more, 0.02 mM or more, 0.03 mM or more, 0.04 mM or more, 0.05 mM or more, 0.06 mM or more, 0.07 mM or more, 0.08 mM or more, 0.09 mM or more, or 0.1 mM or more; and may be 0.5 mM or less, 0.4 mM or less, 0.3 mM or less, 0.2 mM or less, 0.15 mM or less, 0.12 mM or less, 0.1 mM or less, 0.09 mM or less, 0.08 mM or less, 0.07 mM or less, 0.06 mM or less, 0.05 mM or less, 0.04 mM or less, 0.03 mM or less, 0.02 mM or less, or 0.01 mM or less, or may be within a range defined as a non-contradictory combination thereof. The amine concentration in the culture medium may be, in particular, 0.002 mM or more. The amine concentration in the culture medium may be, in more particular, 0.007 mM or more. The amine concentration in the culture medium may be, specifically, for example, 0.002 to 0.5 mM, 0.005 to 0.2 mM, or 0.007 to 0.1 mM.

The choline concentration in the culture medium, for example, may be 0.1 mM or more, 0.2 mM or more, 0.5 mM or more, 1 mM or more, 2 mM or more, 3 mM or more, 4 mM or more, 5 mM or more, 6 mM or more, 7 mM or more, 8 mM or more, 9 mM or more, or 10 mM or more and may be 50 mM or less, 40 mM or less, 30 mM or less, 20 mM or less, 15 mM or less, 12 mM or less, 10 mM or less, 9 mM or less, 8 mM or less, 7 mM or less, 6 mM or less, 5 mM or less, 4 mM or less, 3 mM or less, 2 mM or less, or 1 mM or less, or may be within a range defined as a non-contradictory combination thereof. The choline concentration in the culture medium may be, in particular, 0.2 mM or more. The choline concentration in the culture medium may be, in particular, 1 mM or more. The choline concentration in the culture medium may be, specifically, for example, 0.2 to 50 mM, 0.5 to 20 mM, or 1 to 10 mM.

The serine concentration in the culture medium, for example, may be 0.5 mM or more, 1 mM or more, 2 mM or more, 3 mM or more, 4 mM or more, 5 mM or more, 6 mM or more, 7 mM or more, 8 mM or more, 9 mM or more, 10 mM or more, 12 mM or more, 15 mM or more, 20 mM or more, 25 mM or more, 30 mM or more, 35 mM or more, 40 mM or more, 50 mM or more, 60 mM or more, 70 mM or more, 80 mM or more, 90 mM or more, or 100 mM or more; and may be 500 mM or less, 400 mM or less, 300 mM or less, 200 mM or less, 150 mM or less, 100 mM or less, 70 mM or less, 50 mM or less, 40 mM or less, 30 mM or less, 20 mM or less, 15 mM or less, 12 mM or less, 10 mM or less, 9 mM or less, 8 mM or less, 7 mM or less, 6 mM or less, or 5 mM or less, or may be within a range defined as a non-contradictory combination thereof. The serine concentration in the culture medium may be, in particular, 2 mM or more. The serine concentration in the culture medium may be, in more particular, 10 mM or more. The serine concentration in the culture medium may be, specifically, for example, 1 to 200 mM, 2 to 100 mM, 4 to 50 mM, 2 to 500 mM, 5 to 200 mM, or 10 to 100 mM.

Amine, choline, and/or serine may be present in the culture medium over the whole period of the culture, or may be present in the culture medium during only a partial period of the culture. That is, it is sufficient that the phrase "culture is carried out in the presence of amine, choline, and/or serine" or the phrase "culture is carried out in a culture medium containing amine, choline, and/or serine" means that amine, choline, and/or serine is present in the culture medium during at least a partial period of the culture, and the phrase does not necessary mean that amine, choline, and/or serine is contained in the culture medium over the whole period of the culture.

Amine, choline, and/or serine, for example, may be present in the culture medium at the concentration exemplified above over the whole period of the culture, or may be present in the culture medium at the concentration exemplified above during only a partial period of the culture. That is, it is sufficient that the phrase "culture is carried out in the presence of a certain concentration of amine, choline, and/or serine" or the phrase "culture is carried out in a culture medium having a certain amine concentration, a certain choline concentration, and/or a certain serine concentration" means that the amine concentration, the choline concentration, and/or the serine concentration in the culture medium is within the range of the certain concentration during at least a partial period of the culture, and the phrase does not necessary mean that the amine concentration, the choline concentration, and/or the serine concentration in the culture medium is within the range of the certain concentration over the whole period of the culture.

As for the "partial period", the aforementioned descriptions concerning the "partial period" in the phosphate/potassium-increased conditions can be similarly applied.

The amine concentration, the choline concentration, and/or the serine concentration may be set to the concentration exemplified above, for example, in terms of the average concentration over the whole period of the culture. That is, the phrase "culture is carried out in the presence of a certain concentration of amine, choline, and/or serine" or the phrase "culture is carried out in a culture medium having a certain amine concentration, a certain choline concentration, and/or a certain serine concentration" may also mean that the amine concentration, the choline concentration, and/or the serine concentration in the culture medium in terms of the average concentration over the whole period of the culture is within the range of the certain concentration. The term "the amine concentration, the choline concentration, and/or the serine concentration in the culture medium in terms of the average concentration over the whole period of the culture" is not particularly limited so long as the transition of the amine concentration, the choline concentration, and/or the serine concentration in the culture medium over the whole period of the culture can be recognized, and may refer to, for example, the average of the amine concentrations, the average of the choline concentrations, and/or the average of the serine concentrations in the culture medium measured every 60 minutes, every 30 minutes, every 20 minutes, or every 10 minutes.

The phrase "culture is carried out in the presence of amine, choline, and/or serine" may also mean, for example, that amine, choline, and/or serine is added to the culture medium.

The amount of amine added to the culture medium, for example, may be 0.0002 mM or more, 0.0005 mM or more, 0.001 mM or more, 0.0015 mM or more, 0.002 mM or more, 0.0025 mM or more, 0.003 mM or more, 0.0035 mM or more, 0.004 mM or more, 0.0045 mM or more, or 0.005 mM or more; and may be 0.025 mM or less, 0.02 mM or less, 0.015 mM or less, 0.01 mM or less, 0.007 mM or less, 0.005 mM or less, 0.002 mM or less, or 0.001 mM or less, or may be within a range defined as a non-contradictory combination thereof, per day over the whole period of the culture. The amount of amine added to the culture medium may be, in particular, 0.0005 mM or more per day over the whole period of the culture. The amount of amine added to the culture medium may be, specifically, for example, 0.0005 to 0.025 mM, 0.001 to 0.015 mM, 0.002 to 0.007 mM, or 0.003 to 0.004 mM per day over the whole period of the culture.

The amount of choline added to the culture medium, for example, may be 0.02 mM or more, 0.05 mM or more, 0.1 mM or more, 0.15 mM or more, 0.2 mM or more, 0.25 mM or more, 0.3 mM or more, 0.35 mM or more, 0.4 mM or more, 0.45 mM or more, or 0.5 mM or more; and may be 2.5 mM or less, 2 mM or less, 1.5 mM or less, 1 mM or less, 0.7 mM or less, 0.5 mM or less, 0.2 mM or less, or 0.1 mM or less, or may be within a range defined as a non-contradictory combination thereof, per day over the whole period of the culture. The amount of choline added to the culture medium may be, in particular, 0.05 mM or more per day over the whole period of the culture. The amount of choline added to the culture medium may be, specifically, for example, 0.05 to 2.5 mM, 0.1 to 1.5 mM, 0.2 to 0.7 mM, or 0.3 to 0.5 mM per day over the whole period of the culture.

The amount of serine added to the culture medium, for example, may be 0.1 mM or more, 0.2 mM or more, 0.3 mM or more, 0.4 mM or more, 0.5 mM or more, 0.6 mM or more, 0.7 mM or more, 0.8 mM or more, 0.9 mM or more, 1 mM or more, 1.2 mM or more, 1.5 mM or more, 2 mM or more, 2.5 mM or more, 3 mM or more, 3.5 mM or more, 4 mM or more, 4.5 mM or more, or 5 mM or more; and may be 25 mM or less, 20 mM or less, 15 mM or less, 10 mM or less, 7 mM or less, 5 mM or less, 4 mM or less, 3 mM or less, 2 mM or less, 1 mM or less, 0.7 mM or less, or 0.5 mM or less, or may be within a range defined as a non-contradictory combination thereof, per day over the whole period of the culture. The amount of serine added to the culture medium may be, in particular, 0.5 mM or more per day over the whole period of the culture. The amount of serine added to the culture medium may be, specifically, for example, 0.2 to 10 mM, 0.4 to 5 mM, 0.8 to 3 mM, 0.5 to 25 mM, 1 to 15 mM, 2 to 7 mM, or 3.5 to 5 mM per day over the whole period of the culture.

Amine, choline, and/or serine may be added to the culture medium, for example, continuously or intermittently. Amine, choline, and/or serine may be added to the culture medium, for example, every day or every few days.

When phosphoric acid is added to the culture medium by feeding of the feed medium, the phosphoric acid concentration in the feed medium is not particularly limited, so long as a desired amount of phosphoric acid is attained. The phosphoric acid concentration in the feed medium may be set to, for example, the phosphoric acid concentration in the culture medium exemplified above. The phosphoric acid concentration in the feed medium may be set to, for example, the phosphoric acid concentration in the culture medium exemplified above, for example, when the feed medium is used for perfusion culture. The phosphoric acid concentration in the feed medium, for example, may be a concentration of more than 1 time, 1.1 times or more, 1.3 times or more, 1.5 times or more, 2 times or more, 3 times or more, 5 times or more, 7 times or more, 10 times or more, 15 times or more, or 20 times or more the phosphoric acid concentration in the culture medium exemplified above; and may be a concentration of 100 times or less, 70 times or less, 50 times or less, 30 times or less, 20 times or less, 10 times or less, or 5 times or less the phosphoric acid concentration in the culture medium exemplified above, or may be within a range defined as a non-contradictory combination thereof. The phosphoric acid concentration in the feed medium, for example, may be 10 mM or more, 20 mM or more, 30 mM or more, 50 mM or more, 70 mM or more, 100 mM or more, 150 mM or more, or 200 mM or more; and may be 1000 mM or less, 700 mM or less, 500 mM or less, 300 mM or less, 200 mM or less, 100 mM or less, 70 mM or less, or 50 mM or less, or may be within a range defined as a non-contradictory combination thereof. The phosphoric acid concentration in the feed medium may be, specifically, for example, 10 to 1000 mM, 30 to 500 mM, or 50 to 200 mM.

When amine is added to the culture medium by feeding of the feed medium, the amine concentration in the feed medium is not particularly limited, so long as a desired amount of amine is attained. The amine concentration in the feed medium may be set to, for example, the amine concentration in the culture medium exemplified above. The amine concentration in the feed medium may be set to, for example, the amine concentration in the culture medium exemplified above, for example, when the feed medium is used for perfusion culture. The amine concentration in the feed medium, for example, may be a concentration of more than 1 time, 1.1 times or more, 1.3 times or more, 1.5 times or more, 2 times or more, 3 times or more, 5 times or more, 7 times or more, 10 times or more, 15 times or more, or 20 times or more the amine concentration in the culture medium exemplified above; and may be a concentration of 100 times or less, 70 times or less, 50 times or less, 30 times or less, 20 times or less, 10 times or less, or 5 times or less the amine concentration in the culture medium exemplified above, or may be within a range defined as a non-contradictory combination thereof. The amine concentration in the feed medium, for example, may be 0.05 mM or more, 0.1 mM or more, 0.2 mM or more, 0.3 mM or more, 0.5 mM or more, 0.7 mM or more, 1 mM or more, or 1 mM or more; and may be 5 mM or less, 3 mM or less, 2 mM or less, 1 mM or less, 0.7 mM or less, 0.5 mM or less, 0.3 mM or less, or 0.2 mM or less, or may be within a range defined as a non-contradictory combination thereof. The amine concentration in the feed medium may be, specifically, for example, 0.05 to 5 mM, 0.1 to 3 mM, or 0.2 to 1 mM.

When choline is added to the culture medium by feeding of the feed medium, the choline concentration in the feed medium is not particularly limited, so long as a desired amount of choline is attained. The choline concentration in the feed medium may be set to, for example, the choline concentration in the culture medium exemplified above. The choline concentration in the feed medium may be set to, for example, the choline concentration in the culture medium exemplified above, for example, when the feed medium is used for perfusion culture. The choline concentration in the feed medium, for example, may be a concentration of more than 1 time, 1.1 times or more, 1.3 times or more, 1.5 times or more, 2 times or more, 3 times or more, 5 times or more, 7 times or more, 10 times or more, 15 times or more, or 20 times or more the choline concentration in the culture medium exemplified above; and may be a concentration of 100 times or less, 70 times or less, 50 times or less, 30 times or less, 20 times or less, 10 times or less, or 5 times or less the choline concentration in the culture medium exemplified above, or may be within a range defined as a non-contradictory combination thereof. The choline concentration in the feed medium, for example, may be 5 mM or more, 10 mM or more, 20 mM or more, 30 mM or more, 50 mM or more, 70 mM or more, or 100 mM or more; and may be 500 mM or less, 300 mM or less, 200 mM or less, 100 mM or less, 70 mM or less, 50 mM or less, 30 mM or less, or 20 mM or less, or may be within a range defined as a non-contradictory combination thereof. The choline concentration in the feed medium may be, specifically, for example, 5 to 500 mM, 10 to 300 mM, or 20 to 100 mM.

When serine is added to the culture medium by feeding of the feed medium, the serine concentration in the feed medium is not particularly limited, so long as a desired supply amount of serine is attained. The serine concentration in the feed medium may be set to, for example, the serine concentration in the culture medium exemplified above. The serine concentration in the feed medium may be set to, for example, the serine concentration in the culture medium exemplified above, for example, when the feed medium is used for perfusion culture. The serine concentration in the feed medium, for example, may be a concentration of more than 1 time, 1.1 times or more, 1.3 times or more, 1.5 times or more, 2 times or more, 3 times or more, 5 times or more, 7 times or more, 10 times or more, 15 times or more, or 20 times or more the serine concentration in the culture medium exemplified above and may be a concentration of 100 times or less, 70 times or less, 50 times or less, 30 times or less, 20 times or less, 10 times or less, or 5 times or less the serine concentration in the culture medium exemplified above, or may be within a range defined as a non-contradictory combination thereof. The serine concentration in the feed medium, for example, may be 20 mM or more, 30 mM or more, 50 mM or more, 70 mM or more, 100 mM or more, 200 mM or more, 300 mM or more, 500 mM or more, 700 mM or more, or 1000 mM or more, may be 5000 mM or less, 3000 mM or less, 2000 mM or less, 1000 mM or less, 700 mM or less, 500 mM or less, 300 mM or less, 200 mM or less, 100 mM or less, or 70 mM or less, or may be within a range defined as a non-contradictory combination thereof. The serine concentration in the feed medium may be, specifically, for example, 30 to 2000 mM, 50 to 1000 mM, 70 to 500 mM, 50 to 5000 mM, 100 to 3000 mM, or 200 to 1000 mM.

The concentrations of the various components can be measured by known methods used for detection or identification of compounds. Examples of such methods include, for example, HPLC, UPLC, LC/MS, GC/MS, and NMR. These methods can also be used for confirming generation of the objective substance. One of these methods may be independently used, or two or more of these methods may be used in an appropriate combination.

The animal cells can be cultured as described above. when the animal cells have an objective substance-producing ability such as an objective protein-producing ability, by culturing the animal cells as described above, the objective substance is generated (e.g. the objective protein is expressed) and thereby a culture broth containing the objective substance is obtained. The objective substance such as the objective protein may be accumulated, specifically, in a culture medium, on a cell surface layer, in cells, or in/on a combination thereof.

Hereafter, operations such as confirmation of generation of the objective protein, collection of the objective protein, and purification of the objective protein will be described with reference to cases of producing the objective protein. Such operations can be carried out for the objective substance other than the objective protein as required.

Generation of the objective protein can be confirmed by known methods used for detection or identification of proteins. Examples of such methods include, for example, SDS-PAGE, Western blotting, mass spectrometry, N-terminal amino acid sequence analysis, and enzyme activity measurement. One of these methods may be independently used, or two or more of these methods may be used in an appropriate combination.

The objective protein can be collected as required. Specifically, the objective protein can be collected as an appropriate fraction containing the objective protein. Examples of such a fraction include, for example, a culture broth, a culture supernatant, cultured cells, and a processed product of cultured cells (a disruption product, a lysate, or an extract (cell-free extract)). The cultured cells may also be obtained, for example, in the form of immobilized cells immobilized on a carrier such as acrylamide and carrageenan.

The objective protein may further be purified to a desired extent.

When the objective protein is accumulated in the culture medium, for example, solids such as cells can be removed from the culture broth by centrifugation or the like, and then the objective protein can be purified from the culture supernatant.

When the objective protein is accumulated in cells, for example, the cells can be subject to a treatment such as disruption, lysis, or extraction, and then the objective protein can be purified from the treated product. The cells can be collected from the culture broth by centrifugation or the like. The treatment such as disruption, lysis, or extraction of cells can be carried out by known methods. Examples of such methods include, for example, disruption by ultrasonication, disruption in Dyno-Mill, disruption in bead mill, disruption with French press, and lysozyme treatment. One of these methods may be used alone, or two or more of these methods may be used in combination as required.

When the objective protein is accumulated on a cell surface layer, for example, the objective protein can be solubilized and then separated and purified from the solubilized product. Solubilization can be carried out by known methods. Examples of such methods include, for example, an increase in a salt concentration and use of a surfactant. One of these methods may be independently used, or two or more of these methods may be used in an appropriate combination.

Purification of the objective protein, such as purification of the objective protein from a supernatant, treated product, or solubilized product as described above, can be carried out by known methods used for purification of proteins. Examples of such methods include, for example, ammonium sulfate fractionation, ion exchange chromatography, hydrophobic chromatography, affinity chromatography, gel filtration chromatography, and isoelectric precipitation. One of these methods may be independently used, or two or more of these methods may be used in an appropriate combination.

The objective protein may be obtained in the form of a free enzyme or may be obtained in the form of an immobilized enzyme immobilized on a solid phase such as a resin.

The objective protein collected may be made into a formulation as required. The dosage form of the formulation is not particularly limited and can be appropriately chosen according to various conditions such as use purpose of the objective protein. Examples of the dosage form include, for example, solution, suspension, powder, tablet, pill, and capsule. For preparing such a formulation, for example, pharmaceutically acceptable additives such as excipients, binders, disintegrating agents, lubricants, stabilizers, corrigents, odor-masking agents, perfumes, diluents, and surfactants can be used.

<2> Culture Medium

The culture medium is a culture medium for culturing animal cells, wherein the phosphoric acid concentration and/or the potassium concentration in the culture medium is increased. The culture medium can be used for, for example, the method as described herein.

As for the culture medium, for example, the aforementioned descriptions concerning the culture medium, including the descriptions concerning the feed medium, to be used for the method can be similarly applied.

The culture medium contains phosphoric acid and/or the potassium. The culture medium may further contain amine, choline, and/or serine. The culture medium may further contain amine, choline, and/or serine, for example, when the culture medium at least contains phosphoric acid. The culture medium may contain, for example, at least amine. The culture medium may contain, for example, at least choline and/or serine.

The culture medium may be, for example, a basal medium (starting medium) or a feed medium. The feed medium may be, for example, a feed medium to be used for fed-batch culture or continuous culture. The feed medium may be, for example, in particular, a feed medium to be used for perfusion culture.

As for the phosphoric acid concentration in the culture medium, for example, the aforementioned descriptions concerning the phosphoric acid concentration in the culture medium, including the descriptions concerning the phosphoric acid concentration in the feed medium, in the method can be similarly applied.

As for the potassium concentration in the culture medium, for example, the aforementioned descriptions concerning the potassium concentration in the culture medium, including the descriptions concerning the potassium concentration in the feed medium, in the method can be similarly applied.

As for the amine concentration in the culture medium, for example, the aforementioned descriptions concerning the amine concentration in the culture medium, including the descriptions concerning the amine concentration in the feed medium, in the method can be similarly applied.

As for the choline concentration in the culture medium, for example, the aforementioned descriptions concerning the choline concentration in the culture medium, including the descriptions concerning the choline concentration in the feed medium, in the method can be similarly applied.

As for the serine concentration in the culture medium, for example, the aforementioned descriptions concerning the serine concentration in the culture medium, including the descriptions concerning the serine concentration in the feed medium, in the method can be similarly applied.

EXAMPLES

Hereinafter, the present invention will be more specifically explained with reference to non-limiting examples.

Example 1: Evaluation of Effect of Improving Proliferation of CHO Cells and Antibody Production by Addition of Phosphoric Acid to Feed Medium In this Example, an effect of improving proliferation of CHO cells and antibody production by addition of phosphoric acid to a feed medium was evaluated. As the CHO cells, cells of the CHO DG-44 cell line, that have been modified to produce the antibody Adalimumab.

(1) Preparation of Basal Medium

CELLiST (registered trademark) Basal media (Ajinomoto Co., Ltd.: BASAL4P; containing a final concentration of 1.9 mM phosphoric acid) was added with LR3-IGF-1 (final concentration of 10 μg/mL), dextran sodium sulfate (final concentration of 400 mg/L), and L-Glutamine (final concentration of 6 mM), to prepare a basal medium.

(2) Preparation of Feed Media

CELLiST (registered trademark) Feed media (Ajinomoto Co., Ltd.: FEED2) was added with glucose (final concentration of 75 g/L) and sodium dihydrogen phosphate (final concentration of 0, 125, 250, 500, 1000, 4000, or 7000 mg/L, i.e. 0.0, 1.0, 2.1, 4.2, 8.3, 33.3, or 58.3 mM), to prepare seven feed media having different phosphoric acid concentrations.

(3) Culture Experiment

A 30 mL-aliquot of a CHO cell suspension adjusted to $3 \times 10^5$ cells/mL using the prepared basal medium was seeded into 125 mL-volume flasks (CORNING: 431143) and cultured for 14 days. The culture was carried out with n=2 for all experimental groups. The culture temperature was 37° C. and the agitation speed was 110 rpm. A 2.1 mL-aliquot of each of the prepared feed media was added on days 4, 7, 9, and 11 from the start of the culture. A cell culture broth was sampled on days 4, 7, 9, 11, and 14 from the start of the culture, and the viable cell count was measured using a viable/dead cells autoanalyzer Vi-CELL™ XR (Beckman Coulter), and the antibody production amount was measured using Octet QK (FORTEBIO).

(4) Culture Results

Figure 2:
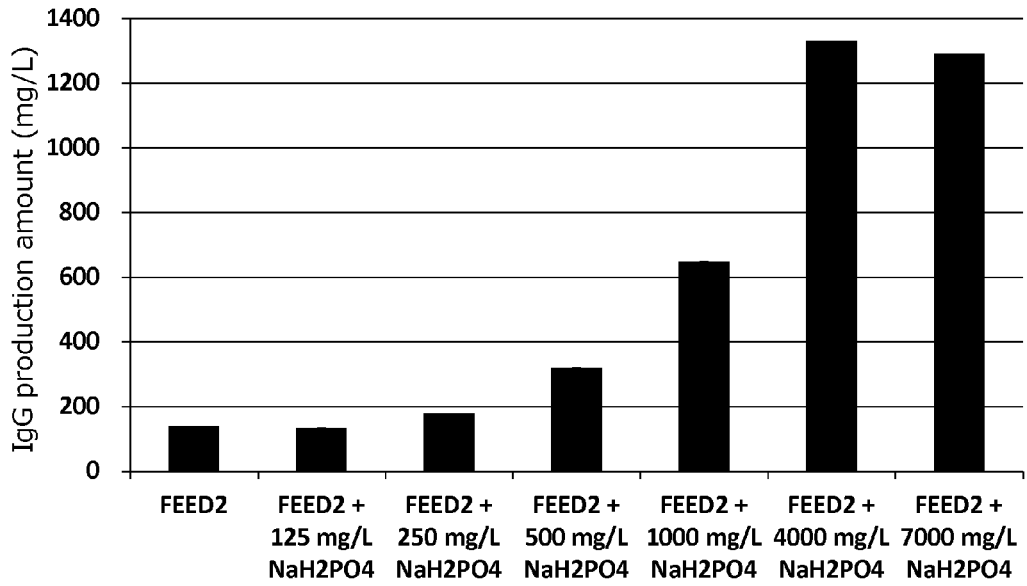
FIG. 2 depicts a diagram showing the effect of the concentration of phosphoric acid in a feed medium on antibody production by CHO cells.

Transition of the viable cell counts and the antibody production amounts on day 14 of culture are shown in FIGS. 1 and 2. It was revealed that the viable cell count and the antibody production amount are increased with increasing the phosphoric acid concentration in the feed medium.

Example 2: Evaluation of Effect of Improving Proliferation of CHO Cells and Antibody Production by Addition of Phosphoric Acid to Feed Medium In this Example, an effect of improving proliferation of CHO cells and antibody production by addition of phosphoric acid to a feed medium was evaluated. As the CHO cells, cells of the CHO DG-44 cell line, that have been modified to produce the antibody Adalimumab.

(1) Preparation of Basal Medium

CELLiST (registered trademark) Basal media (Ajinomoto Co., Ltd.: BASAL4P; containing a final concentration of 1.9 mM phosphoric acid) was added with LR3-IGF-1 (final concentration of 10 μg/mL), sodium dihydrogen phosphate (115 mg/L, i.e. final concentration of 2.9 mM), dextran sodium sulfate (final concentration of 400 mg/L), and L-Glutamine (final concentration of 6 mM), to prepare a basal medium.

(2) Preparation of Feed Media

CELLiST (registered trademark) Feed media (Ajinomoto Co., Ltd.: FEED2) was added with glucose (final concentration of 75 g/L) and sodium dihydrogen phosphate (final concentration of 0, 1000, 2000, 3000, 4000, or 5000 mg/L, i.e. 0.0, 8.3, 16.7, 25, 33.3, or 41.7 mM), to prepare six feed media having different phosphoric acid concentrations.

(3) Culture Experiment

A 30 mL-aliquot of a CHO cell suspension adjusted to $3 \times 10^5$ cells/mL using the prepared basal medium was seeded into 125 mL-volume flasks (CORNING: 431143) and cultured for 14 days. The culture was carried out with n=2 for all experimental groups. The culture temperature was 37° C. and the agitation speed was 110 rpm. A 2.1 mL-aliquot of each of the prepared feed media was added on days 4, 7, 9, and 11 from the start of the culture. A cell culture broth was sampled on days 4, 7, 9, 11, and 14 from the start of the culture, and the viable cell count was measured using a viable/dead cells autoanalyzer Vi-CELL™ XR (Beckman Coulter), and the antibody production amount was measured using CEDEX Bio HT (Roche Diagnostics).

(4) Culture Results

Figure 3:
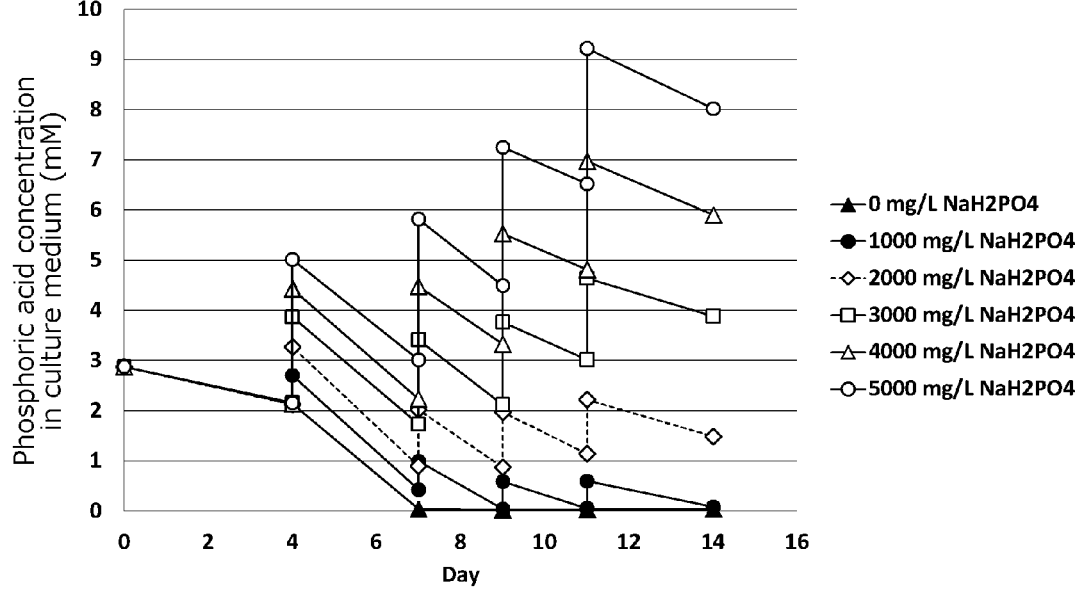
FIG. 3 depicts a diagram showing the transition of the concentration of phosphoric acid in a culture medium.
Figure 4:
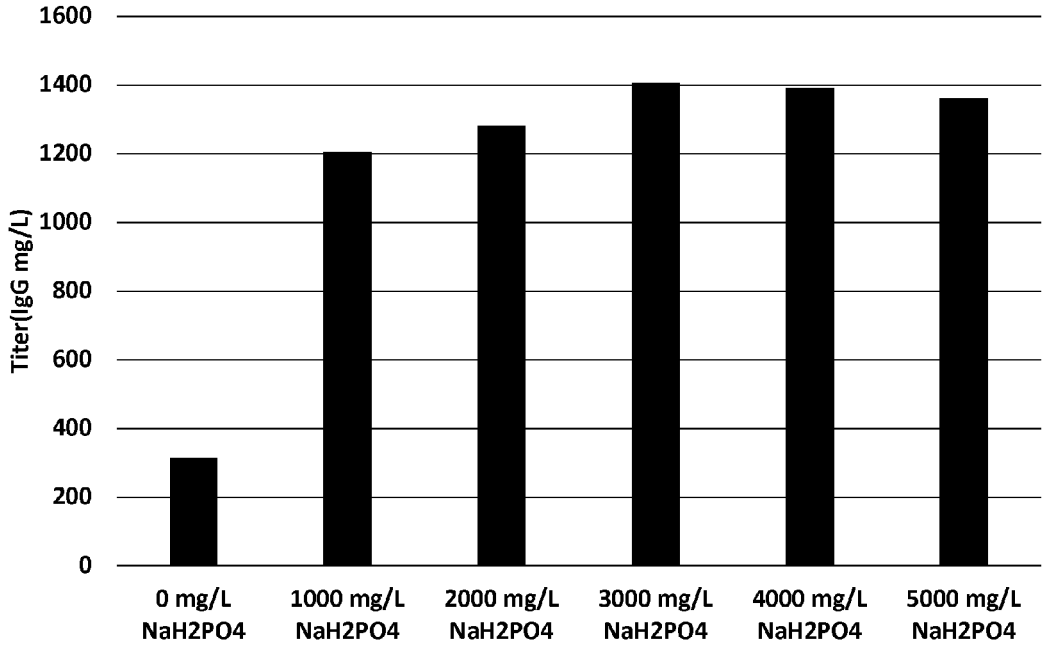
FIG. 4 depicts a diagram showing the effect of the concentration of phosphoric acid in a feed medium on antibody production by CHO cells.

Transition of the phosphoric acid concentration in the culture medium and the antibody production amounts on day 14 of culture are shown in FIGS. 3 and 4. The phosphoric acid concentration (1.5 to 3.5 mM phosphoric acid concentration in the culture medium) described in a prior patent (U.S. Pat. No. 6,924,124) was reproduced by adding the feed medium containing a final concentration of 2000 mg/L sodium dihydrogen phosphate. It was revealed that the antibody productivity is improved as compared with that observed under the conditions of the prior patent by adding the feed medium containing a higher concentration of phosphoric acid than the conditions of the prior patent.

Example 3: Evaluation of Effect of Improving Proliferation of CHO Cells and Antibody Production by Addition of Phosphoric Acid in Combination with Serine, Choline, or Amine to Feed Medium In this Example, an effect of improving proliferation of CHO cells and antibody production by addition of phosphoric acid in combination with serine, choline, or amine to a feed medium was evaluated. As the CHO cells, cells of the CHO S cell line, that have been modified to produce an antibody Adalimumab.

(1) Preparation of Basal Medium

CELLiST (registered trademark) Basal media (Ajinomoto Co., Ltd.: BASAL4P; containing a final concentration of 1.9 mM phosphoric acid) was added with LR3-IGF-1 (final concentration of 10 μg/mL), sodium dihydrogen phosphate (115 mg/L, i.e. final concentration of 2.9 mM in terms of the total concentration with phosphoric acid contained in Basal media), dextran sodium sulfate (final concentration of 400 mg/L), and L-Glutamine (final concentration of 6 mM), to prepare a basal medium.

(2) Preparation of Feed Media

CELLiST (registered trademark) Feed media (Ajinomoto Co., Ltd.: FEED2) was added with glucose (final concentration of 75 g/L), sodium dihydrogen phosphate (final concentration of 0 or 2500 mg/L, i.e. 0.0 or 20.8 mM), and the following component(s) (A), (B), (C), or (D) as required, to prepare ten feed media:

(A) 1,4-butanediamine (final concentration of 12.8 mg/L, i.e. 0.145 mM);

(B) serine (final concentration of 20,000 mg/L, i.e. 190 mM), choline bitartrate (final concentration of 4,400 mg/L, i.e. 17.4 mM), and 1,4-butanediamine (final concentration of 12.8 mg/L, i.e. 0.145 mM);

(C) the components (B) at concentrations of 1.5 times the concentrations in (B) (i.e. serine, 30,000 mg/L; choline bitartrate, 6,600 mg/L; and 1,4-butanediamine, 19.2 mg/L);

(D) the components (B) at concentrations of 2 times the concentrations in (B) (i.e. serine, 40,000 mg/L; choline bitartrate, 8,800 mg/L; and 1,4-butanediamine, 25.6 mg/L).

(3) Culture Experiment

A CHO cell suspension adjusted to $3 \times 10^5$ cells/mL using the prepared basal medium was seeded into 4 mL-volume 6-well flasks (CORNING: 3471) and cultured for 14 days. The culture was carried out with n=2 for all experimental groups. The culture temperature was 37° C. and the agitation speed was 110 rpm. A 280 μL-aliquot of each of the prepared feed media was added on days 4, 7, 9, and 11 from the start of the culture. A cell culture broth was sampled on days 4, 7, 9, 11, and 14 from the start of the culture, and the viable cell count was measured using a flow cytometer guava easyCyte (Luminex), and the antibody production amount was measured using CEDEX Bio HT (Roche Diagnostics).

(4) Culture Results

Figure 5:
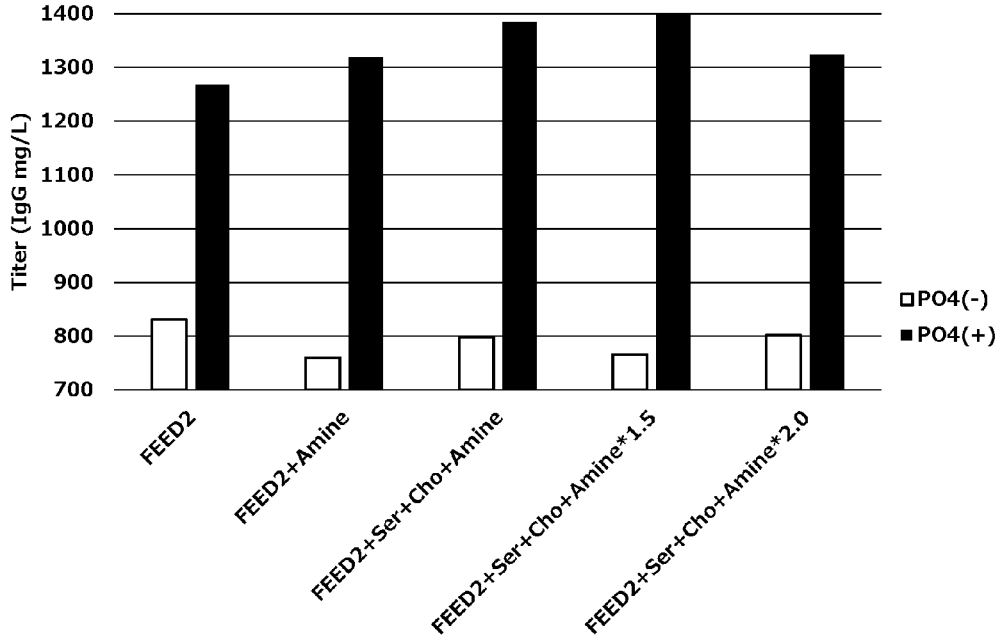
FIG. 5 depicts a diagram showing the effect of the concentrations of phosphoric acid, amine, choline, and serine in a feed medium on antibody production by CHO cells.

The antibody production amounts on day 14 of culture are shown in FIG. 5. Under the conditions of not adding sodium dihydrogen phosphate to the feed medium, no effect by addition of serine, choline bitartrate, or 1,4-butanediamine was observed. By contrast, it was revealed that, under the conditions of adding sodium dihydrogen phosphate to the feed medium, the antibody productivity is improved by addition of 1,4-butanediamine, and the antibody productivity is further improved by addition of serine, choline bitartrate, and 1,4-butanediamine. In particular, the maximum antibody concentration was observed when serine, choline bitartrate, and 1,4-butanediamine were added at 1.5-fold concentrations.

Example 4: Evaluation of Effect of Improving Proliferation of CHO Cells and Antibody Production by Addition of Phosphoric Acid or Potassium to Feed Medium In this Example, an effect of improving proliferation of CHO cells and antibody production by addition of phosphoric acid or potassium to a feed medium was evaluated. As the CHO cells, cells of the CHO S cell line, that have been modified to produce an antibody Herceptin.

(1) Preparation of Basal Medium

CELLiST (registered trademark) Basal media (Ajinomoto Co., Ltd.: BASAL3; containing a final concentration of 1.9 mM phosphoric acid) was added with LR3-IGF-1 (final concentration of 10 μg/mL) and L-Glutamine (final concentration of 6 mM), to prepare a basal medium.

(2) Preparation of Feed Media

CELLiST (registered trademark) Feed media (Ajinomoto: FEED2) was added with disodium hydrogen phosphate (final concentration of 0 or 4,510 mg/L, i.e. 0.0 or 20.8 mM) and potassium chloride (final concentration of 0 or 2,850 mg/L, i.e. 0.0 or 38.2 mM), to prepare four feed media.

(3) Culture Experiment

A 30 mL-aliquot of a CHO cell suspension adjusted to $3 \times 10^5$ cells/mL using the prepared basal medium was seeded into 125 mL-volume flasks (CORNING: 431143) and cultured for 14 days. The culture was carried out with n=2 for all experimental groups. The culture temperature was 37° C. and the agitation speed was 110 rpm. A 1.2 mL-aliquot of each of the prepared feed media was added on days 4, 6, 8, 10, and 12 from the start of the culture. A cell culture broth was sampled on days 4, 7, 9, 11, and 14 from the start of the culture, and the viable cell count was measured using a viable/dead cells autoanalyzer Vi-CELL™ XR (Beckman Coulter), and the antibody production amount was measured using CEDEX Bio HT (Roche Diagnostics). In addition, a cell culture broth was sampled on days 4, 7, 9, and 11 from the start of the culture, the glucose concentration was measured using CEDEX Bio HT (Roche Diagnostics), and 500 g/L glucose aqueous solution was added so that the final concentration of glucose became 11 g/L.

(4) Culture Results

Figure 6:
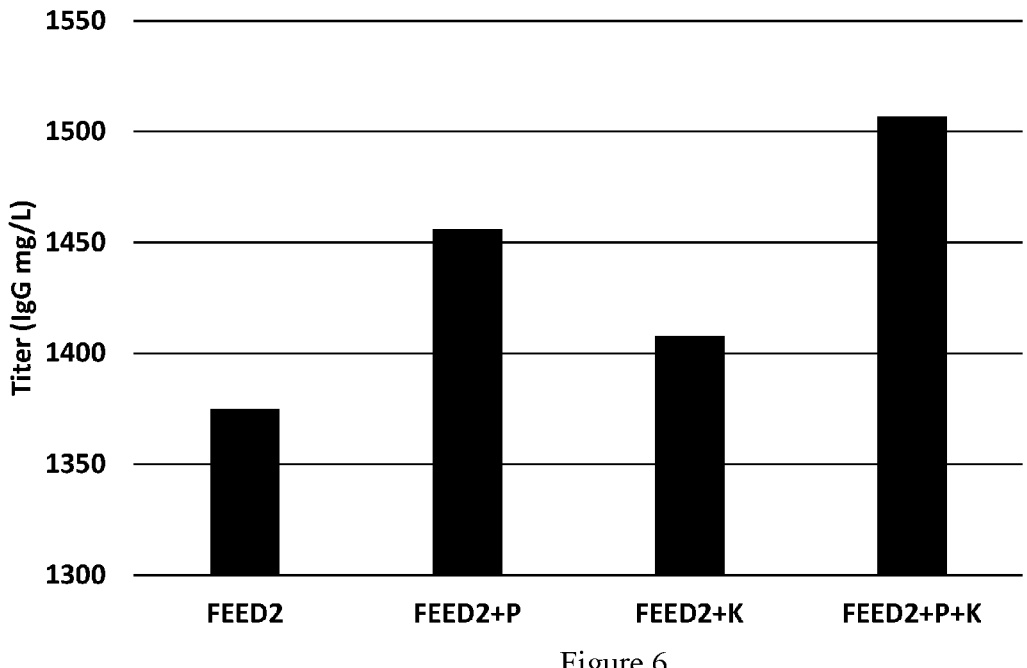
FIG. 6 depicts a diagram showing the effect of the concentrations of phosphoric acid and potassium in a feed medium on antibody production by CHO cells.

The antibody production amounts on day 14 of culture are shown in FIG. 6. The group with phosphoric acid and/or potassium added to the feed medium provided a higher value of the antibody production amount than that observed for the group with no addition. In addition, the group with phosphoric acid and potassium added provided a higher value of the antibody production amount than those observed for the group with phosphoric acid solely added and the group with potassium solely added.

Example 5: Evaluation of Effect of Improving Antibody Production by Phosphoric Acid-Enriched Media in Perfusion Culture In this Example, an effect of improving proliferation of CHO cells and antibody production by addition of phosphoric acid to a basal medium and a feed medium was evaluated in perfusion culture. As the CHO cells, cells of the CHO S cell line, that have been modified to produce the antibody Adalimumab.

(1) Preparation of Basal Media and Feed Media

CELLiST (registered trademark) Basal media (Ajinomoto Co., Ltd.: BASAL4P; containing a final concentration of 1.9 mM phosphoric acid) was added with LR3-IGF-1 (final concentration of 10 μg/mL), sodium dihydrogen phosphate (addition amount of 0, 1450, or 1690 mg/L, i.e. final concentration of 1.9, 14, or 16 mM in terms of the total concentration with phosphoric acid contained in Basal media), and L-Glutamine (final concentration of 6 mM), to prepare basal media and feed media.

.

(2) Culture Experiment

A 10 mL-aliquot of a CHO cell suspension adjusted to $25×10^5$ cells/mL using each of the prepared basal media was cultured for 8 days using a micro bioreactor ambr15 (sartorius: 001-0881). During the culture, pH 7.2±0.1, DO at 50% of the saturation concentration, the culture temperature at 37° C., and the agitation speed at 1000 rpm were maintained. After the cell count reached $200×10^5$ cells/mL, the cell count was measured every day, the excess cell culture broth was removed so that the cell concentration in the culture medium after medium exchange became $200×10^5$ cells/mL, and then the medium exchange was carried out. The medium exchange was carried out by centrifuging the culture broth, removing the centrifugal supernatant so that 3.68 mL of the same was left, adding 6.32 mL of a fresh feed medium identical to the basal medium, and stirring the resultant. After the medium exchange, the culture was resumed. The viable cell count was measured using a viable/dead cells autoanalyzer Vi-CELL™ XR (Beckman Coulter), and the antibody production amount was measured using CEDEX Bio HT (Roche Diagnostics).

(3) Culture Results

Figure 7:
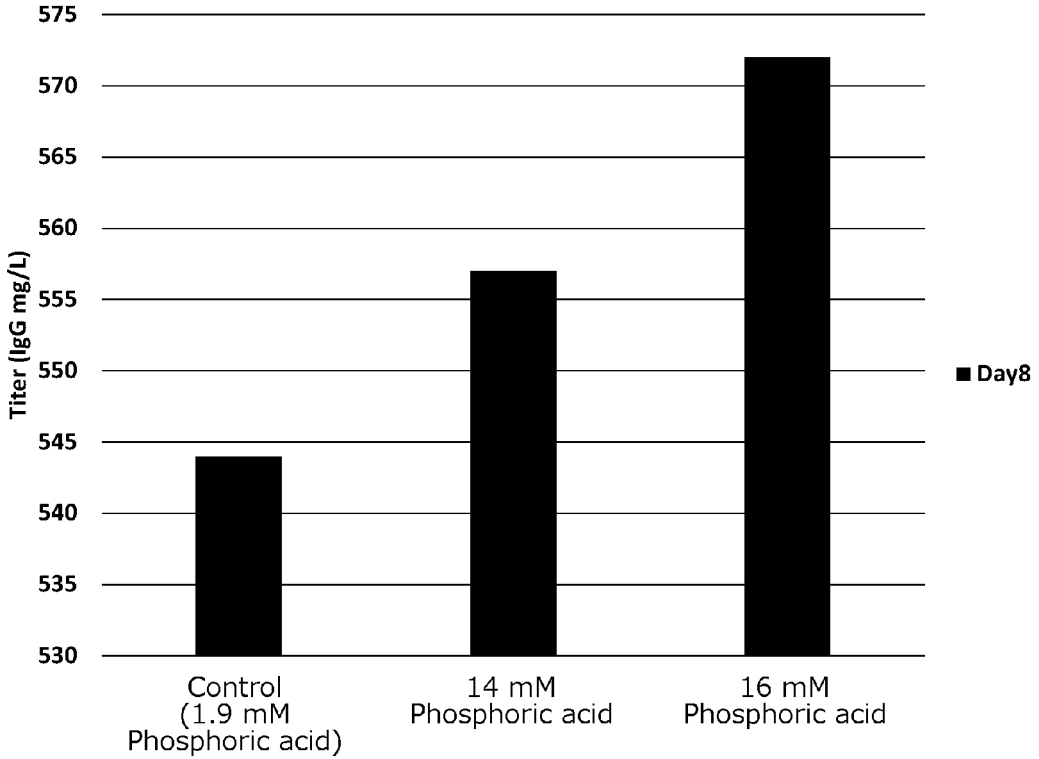
FIG. 7 depicts a diagram showing the effect of the concentration of phosphoric acid in a basal medium and a feed medium on antibody production by CHO cells in a perfusion culture.

The antibody production amounts on day 8 of culture are shown in FIG. 7. It was revealed that the antibody concentration is increased when enhancing the phosphoric acid concentration in the basal medium and the feed medium to be 14 mM or more as compared with when not enhancing the phosphoric acid concentration in the basal medium or the feed medium.

Example 6: Evaluation of Effect of Improving Antibody Production by Phosphoric Acid-Enriched Media in Perfusion Culture In this Example, an effect of improving proliferation of CHO cells and antibody production by addition of phosphoric acid to a feed medium was evaluated in perfusion culture. As the CHO cells, cells of the CHO S cell line, that have been modified to produce an antibody Adalimumab.

(1) Preparation of Basal Medium

CELLiST (registered trademark) Basal media (Ajinomoto Co., Ltd.: BASAL4P; containing a final concentration of 1.9 mM phosphoric acid) was added with LR3-IGF-1 (final concentration of 10 μg/mL) and L-Glutamine (final concentration of 6 mM), to prepare a basal medium.

(2) Preparation of Feed Media

CELLiST (registered trademark) Basal media (Ajinomoto Co., Ltd.: BASAL4P; containing a final concentration of 1.9 mM phosphoric acid) was added with LR3-IGF-1 (final concentration of 10 μg/mL), sodium dihydrogen phosphate (addition amount of 0, 490, or 730 mg/L, i.e. final concentration of 1.9, 6, or 8 mM in terms of the total concentration with phosphoric acid contained in Basal media), and L-Glutamine (final concentration of 6 mM), to prepare feed media.

(3) Culture Experiment

A 10 mL-aliquot of a CHO cell suspension adjusted to $25×10^5$ cells/mL using each of the prepared basal media was cultured for 12 days using a micro bioreactor ambr15 (sartorius: 001-0881). During the culture, pH 7.2±0.1, DO at 50% of the saturation concentration, the culture temperature at 37° C., and the agitation speed at 1000 rpm were maintained. After the cell count reached $150×10^5$ cells/mL, the cell count was measured every day, the excess cell culture broth was removed so that the cell concentration in the culture medium after medium exchange became $150×10^5$ cells/mL, and then the medium exchange was carried out. The medium exchange was carried out by centrifuging the culture broth, removing the centrifugal supernatant so that 3.68 mL of the same was left, and adding 6.32 mL of a fresh feed medium. After the medium exchange, the culture was resumed. The viable cell count was measured using a viable/dead cells autoanalyzer Vi-CELL™ XR (Beckman Coulter), and the antibody production amount was measured using CEDEX Bio HT (Roche Diagnostics).

(4) Culture Results

Figure 8:
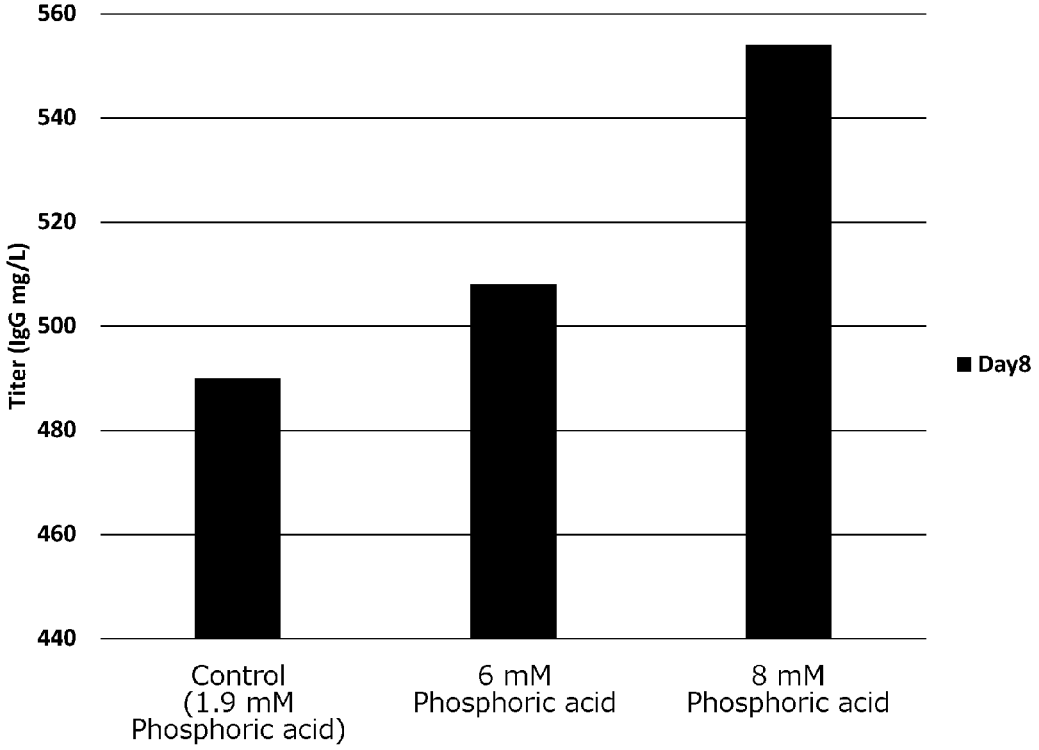
FIG. 8 depicts a diagram showing the effect of the concentration of phosphoric acid in a feed medium on antibody production by CHO cells in a perfusion culture.

The antibody production amounts on day 8 of culture are shown in FIG. 8. It was revealed that the antibody concentration is increased when enhancing the phosphoric acid concentration in the feed medium to be 6 mM or more as compared with when not enhancing the phosphoric acid concentration in the feed medium.

INDUSTRIAL APPLICABILITY

According to the present invention, the culture performance of animal cells (e.g. proliferation of animal cells and production of an objective substance by animal cells) can be improved.

The invention claimed is:

1. A method for producing an objective substance, the method comprising:

culturing animal cells having an objective substance-producing ability in a culture medium; and collecting the objective substance, wherein the culturing is carried out under the following condition:

(A) a phosphoric acid concentration in the culture medium is increased to be 5 mM or more; and/or (B) a phosphoric acid concentration in the culture medium is increased to be 5 mM or more and a potassium concentration in the culture medium is increased to be 1 mM or more.

2. The method according to claim 1, wherein the objective substance is a protein.

3. A method for culturing animal cells, the method comprising:

culturing the animal cells in a culture medium, wherein the culturing is carried out under the following condition:

(A) a phosphoric acid concentration in the culture medium is increased to be 5 mM or more; or (B) a phosphoric acid concentration in the culture medium is increased to be 5 mM or more and a potassium concentration in the culture medium is increased to be 1 mM or more.

4. The method according to claim 1, wherein the phosphoric acid concentration in the culture medium during the culturing 6 mM or more.

5. The method according to claim 1, wherein the phosphoric acid concentration in the culture medium during the culturing is 11 mM or more.

6. The method according to claim 1, wherein the phosphoric acid and/or potassium is present in the culture medium at said concentration at the start of the culturing.

7. The method according to claim 1, wherein the phosphoric acid and/or potassium is added to the culture medium after the start of the culturing so to be present in the culture medium at said concentration.

8. The method according to claim 1, wherein said concentration of the phosphoric acid and/or potassium in the culture medium is an average concentration over the whole period of the culturing.

9. The method according to claim 1, wherein 0.05 mM or more of phosphoric acid is added to the culture medium per day over the whole period of the culturing.

10. The method according to claim 1, wherein 0.5 mM or more of phosphoric acid is added to the culture medium per day over the whole period of the culturing.

11. The method according to claim 1, wherein 0.2 mM or more of potassium is added to the culture medium per day over the whole period of the culturing.

12. The method according to claim 1, wherein the culturing is a perfusion culture using a feed medium having a phosphoric acid concentration of 11 mM or more.

13. The method according to claim 1, wherein the culturing is carried out in the presence of amine, choline, and/or serine.

14. The method according to claim 13, wherein the amine is 1,4-butanediamine.

15. The method according to claim 13, wherein the amine concentration in the culture medium during the culturing is 0.002 mM or more, the choline concentration in the culture medium during the culturing is 0.2 mM or more, and/or the serine concentration in the culture medium during the culturing is 2 mM or more.

16. The method according to claim 13, wherein the amine concentration in the culture medium during the culturing is 0.007 mM or more, the choline concentration in the culture medium during the culturing is 0.2 mM or more, and/or the serine concentration in the culture medium during the culturing is 2 mM or more.

17. The method according to claim 15, wherein the amine, choline, and/or serine is present in the culture medium at said concentration at the start of the culturing.

18. The method according to claim 15, wherein the amine, choline, and/or serine is added to the culture medium after the start of the culturing so to be present in the culture medium at said concentration.

19. The method according to claim 15, wherein said concentrations of each of the amine, choline, and/or serine in the culture medium are average concentrations over the whole period of the culturing.

20. The method according to claim 13, wherein 0.0005 mM or more of amine is added to the culture medium per day over the whole period of the culturing.

21. The method according to claim 13, wherein 0.05 mM or more of choline is added to the culture medium per day over the whole period of the culturing.

22. The method according to claim 13, wherein 0.5 mM or more of serine is added to the culture medium per day over the whole period of the culturing.

* * * * *